United States Patent
Semba

(10) Patent No.: US 10,630,879 B2
(45) Date of Patent: Apr. 21, 2020

(54) IMAGING CONTROL DEVICE, IMAGING APPARATUS, IMAGING CONTROL SYSTEM, IMAGE DISPLAY APPARATUS, IMAGING CONTROL METHOD, INFORMATION PROCESSING METHOD, AND PROGRAM

(71) Applicant: CANON KABUSHIKI KAISHA, Tokyo (JP)

(72) Inventor: Daiya Semba, Inagi (JP)

(73) Assignee: Canon Kabushiki Kaisha, Tokyo (JP)

(*) Notice: Subject to any disclaimer, the term of this patent is extended or adjusted under 35 U.S.C. 154(b) by 44 days.

(21) Appl. No.: 15/362,671

(22) Filed: Nov. 28, 2016

(65) Prior Publication Data

US 2017/0163869 A1    Jun. 8, 2017

(30) Foreign Application Priority Data

Dec. 3, 2015 (JP) .................. 2015-236743

(51) Int. Cl.
| | | |
|---|---|---|
| *H04N 5/232* | (2006.01) | |
| *A61B 6/00* | (2006.01) | |
| *H04N 5/445* | (2011.01) | |
| *H04N 5/44* | (2011.01) | |
| *H04N 5/32* | (2006.01) | |
| *G06F 19/00* | (2018.01) | |

(52) U.S. Cl.
CPC ......... *H04N 5/23206* (2013.01); *A61B 6/465* (2013.01); *A61B 6/563* (2013.01); *G06F 19/321* (2013.01); *H04N 5/23216* (2013.01); *H04N 5/23293* (2013.01); *H04N 5/4403* (2013.01); *H04N 5/44591* (2013.01); *H04N 5/232* (2013.01); *H04N 5/32* (2013.01)

(58) Field of Classification Search
CPC .......................... G06F 19/321; H04N 5/23206
See application file for complete search history.

(56) References Cited

U.S. PATENT DOCUMENTS

| | | | | |
|---|---|---|---|---|
| 2007/0036268 | A1* | 2/2007 | Matsuno | A61B 6/00 378/98.2 |
| 2014/0072192 | A1* | 3/2014 | Reiner | G06T 7/0012 382/128 |
| 2016/0350480 | A1* | 12/2016 | Gerdeman | G06F 19/321 |

FOREIGN PATENT DOCUMENTS

| | | |
|---|---|---|
| JP | 2004-097783 A | 4/2004 |
| JP | 2006-51198 A | 2/2006 |
| JP | 2011-255055 A | 12/2011 |
| JP | 2012-130369 A | 7/2012 |
| JP | 2014-083123 A | 5/2014 |

* cited by examiner

*Primary Examiner* — Christopher K Peterson
(74) *Attorney, Agent, or Firm* — Canon U.S.A., Inc., IP Division

(57) ABSTRACT

An imaging control device acquires examination order information, outputs, external to the imaging control device, a captured image obtained based on a first imaging protocol information included in the examination order information, and acquires second imaging protocol information for additional imaging based on an instruction from an external apparatus that received the output captured image.

16 Claims, 28 Drawing Sheets

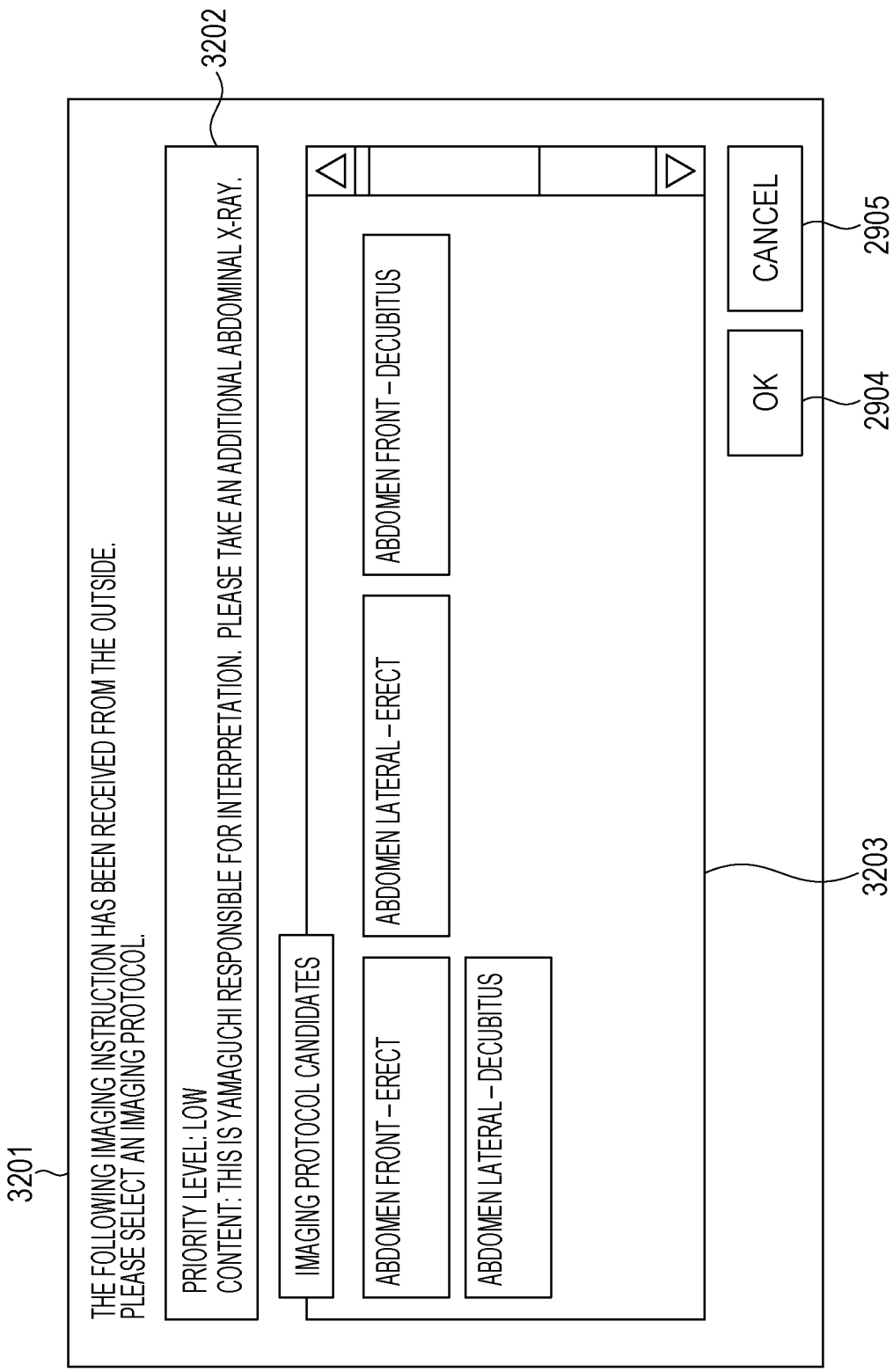

IMAGING CONTROL DEVICE, IMAGING APPARATUS, IMAGING CONTROL SYSTEM, IMAGE DISPLAY APPARATUS, IMAGING CONTROL METHOD, INFORMATION PROCESSING METHOD, AND PROGRAM

BACKGROUND

Field

The disclosure of the present specification relates to an imaging control device, an imaging apparatus, an imaging control system, an image display apparatus, an imaging control method, an information processing method, and a program.

Description of the Related Art

In recent years, a medical information system where a plurality of apparatuses is connected in a communication network is constructed in a medical institution. For example, in a case of X-ray imaging, an examination instruction is input from an HIS (Hospital Information System) terminal or a RIS (Radiology Information System) terminal to be conveyed to a radiological department being a requestee. These network communications are achieved by a technical framework based on, for example, medical standard guidelines of IHE (Integrating the Healthcare Enterprise).

Request information registered in the HIS or RIS is called an examination order. The examination order includes the name of a department of a requestor, an examination requested, and personal data of a patient. In the X-ray imaging system, imaging protocol information including various conditions for imaging is obtained in accordance with such an examination order. The imaging protocol information is information including an imaging region and imaging method requested by a doctor, and image processing information. An examination proceeds in accordance with a plurality of pieces of the obtained imaging protocol information. An image obtained by imaging is transferred to, for example, an image quality checking terminal.

The transferred captured image is displayed on a screen of the image quality checking terminal. An examination technologist views the image to determine whether it is of quality suitable for interpretation by a doctor. If having determined that it is suitable for interpretation, the examination technologist transfers the captured image to a medical image management system called a PACS (Picture Archiving and Communication System) and saves it. Japanese Patent Laid-Open No. 2006-51198 discloses that upon having determined that a captured image is not suitable for interpretation, the captured image is not transferred to a PACS and a message is transmitted which instructs of re-imaging a radiologic technologist who is responsible for the operation of the X-ray imaging system.

If additional imaging is instructed for a given examination from a terminal for image checks outside an imaging apparatus, additional imaging may not be performed appropriately for reasons of an ambiguous content of such an instruction.

SUMMARY

An imaging control device according to one embodiment of the disclosure includes: an examination acquisition unit configured to acquire examination order information including first imaging protocol information including at least imaging region information, an imaging condition, an irradiation condition, an image processing condition, or an output condition; an output unit configured to output, external to the imaging control device, a captured image obtained based on the first imaging protocol information; and an additional protocol acquisition unit configured to acquire second imaging protocol information for additional imaging based on an instruction from an external apparatus that received the output captured image.

Further features will become apparent from the following description of exemplary embodiments with reference to the attached drawings.

BRIEF DESCRIPTION OF THE DRAWINGS

FIG. 32 is a diagram illustrating an example of an imaging protocol information selection screen according to the sixth embodiment.

DESCRIPTION OF THE EMBODIMENTS

Embodiments of a radiographic imaging system and a processing method thereof are described in detail hereinafter with reference to the accompanying drawings. In the following embodiments, a description is given taking an example of a case where X-rays are applied as radiation. Radiation is not limited to X-rays, and can be, for example, electromagnetic waves, α rays, β rays, or γ rays.

First Embodiment

An example of an imaging system according to an embodiment is described. Such an imaging system is a system that obtains a captured image of a subject, and has the following functions. In other words, imaging information (an examination order) including first imaging protocol information including at least imaging region information, imaging conditions, irradiation conditions, image processing conditions, or output conditions, and examinee information for imaging related to the imaging information are displayed on a display unit. A captured image obtained based on the first imaging protocol information included in the imaging information is output external to the imaging system. Second imaging protocol information for additional imaging based on an instruction of an external apparatus that has received the output captured image is then acquired. The second imaging protocol information, together with the first imaging protocol information included in the imaging information, is displayed.

Such functions are achieved by, for example, a CPU (Central Processing Unit) described below, a memory where a program to be executed by the CPU is stored, a RAM (Random Access Memory) where the program is developed to be executed by the CPU, and a communication circuit that is controlled by the CPU.

Such functions allow additional imaging for given imaging information to be executed at an instruction of a device that has received the captured image. In addition, the protocol information for additional imaging based on such an instruction is acquired to be displayed with the existing imaging protocol information. Accordingly, it saves time and effort to set or check various conditions included in the imaging protocol information, which contributes to facilitation or quick execution of the additional imaging.

The operation of the imaging system according to the embodiment and the above-mentioned functions of such a system are described in detail below taking a specific example of the system.

Figure 1:
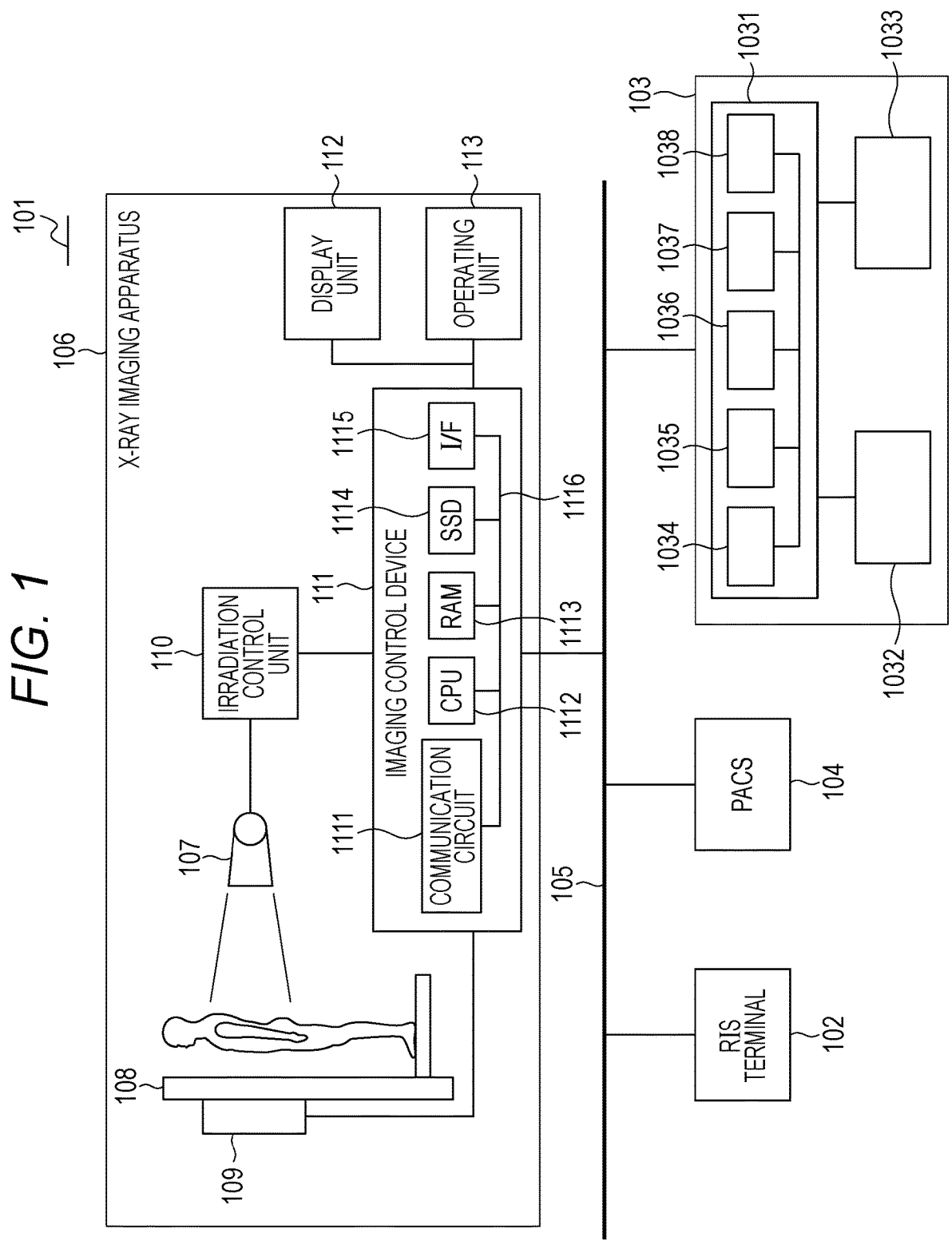
FIG. 1 is a diagram illustrating an example of an X-ray imaging system 101 to which a radiographic imaging system is applied according to first to sixth embodiments.

FIG. 1 is a diagram illustrating an X-ray imaging system 101 being an example of the imaging system.

The X-ray imaging system 101 is configured including a RIS terminal 102, an image quality assurance terminal 103, a PACS 104, and an X-ray imaging apparatus 106. These apparatuses are connected via a communication network 105 such as an internal or external network.

The RIS terminal 102 is an information system in a radiological department. The X-ray imaging apparatus 106 captures an X-ray digital image (hereinafter referred to as captured image). The PACS 104 saves and manages the captured image captured by the X-ray imaging apparatus 106. The image quality assurance terminal 103 is an image display apparatus that displays the captured image captured by the X-ray imaging apparatus 106.

The image quality assurance terminal 103 receives, from the X-ray imaging apparatus 106, imaging information including a captured image and examinee information of the captured image, and displays the received captured image on a display unit. The image quality assurance terminal 103 transmits, to the X-ray imaging apparatus 106, information related to additional imaging for imaging related to the imaging information in response to the input of an operation of instructing the additional imaging. The information related to the additional imaging includes, for example, at least instruction information including at least imaging region information, imaging conditions, irradiation conditions, image processing conditions, or output conditions, and an identification ID of the imaging information, or instruction information of an image ID of the captured image. Such functions allow the transmission of an additional imaging instruction from the image quality assurance terminal 103 capable of displaying the captured image to the X-ray imaging apparatus 106.

As illustrated in, for example, FIG. 1, the image quality assurance terminal 103 includes a terminal control unit 1031, a terminal display unit 1032, and a terminal operating unit 1033. The terminal control unit 1031 further includes a terminal communication circuit 1034, a terminal CPU 1035, a terminal RAM 1036, a terminal SSD 1037, and a terminal I/F 1038. A computer program stored in the terminal SSD 1037 is developed in the terminal RAM 1036 to have the terminal CPU 1035 execute the computer program. Accordingly, the above-mentioned functions are achieved by processing performed mainly by the terminal CPU 1035 and the terminal communication circuit 1034. The details of information processing with such a configuration are described below with reference to a flowchart described in FIG. 6.

The X-ray imaging apparatus 106 advances an examination (imaging) based on an examination order (imaging information) composed of a plurality of pieces of imaging protocol information. Each piece of the imaging protocol information specifies imaging conditions, the content of image processing to be executed on a captured image, and the like. More specifically, for example, information on various parameters for imaging, image processing, and the like, and imaging performed information are included. Furthermore, imaging environment information (the type of sensor and imaging position) is associated.

The X-ray imaging apparatus 106 is configured including an X-ray tube 107, an imaging platform 108, a sensor 109, an irradiation control unit 110, an imaging control device 111, a display unit 112, and an operating unit 113.

The X-ray tube 107 functions as an irradiation unit that irradiates a subject (an examinee being an examination target) with X-rays. The irradiation control unit 110 controls the generation of X-rays based on imaging protocol information. Specifically, a voltage is applied to the X-ray tube 107 based on imaging conditions (for example, parameters of a tube current, a tube voltage, and irradiation duration) corresponding to the imaging protocol information to generate X-rays.

The imaging platform 108 functions as a holding unit that holds the sensor 109 for imaging. Alternatively, the imaging platform 108 functions as an adjustment unit that adjusts the positional relationship between the sensor 109 and the examinee.

The sensor 109 functions as a radiation detecting unit, and is an imaging unit that detects X-rays having passed through the examinee to acquire an X-ray image. Included are an A/D conversion unit that performs an A/D conversion on electric charge corresponding to the transmitted X-ray dosage of the examinee detected by the sensor 109, and a communication circuit that transfers the digital output as a captured image to the imaging control device 111.

The display unit 112 includes, for example, a display, and displays a system status and the like for an operator. For example, an examination order received from the RIS terminal 102 (or an examination order created by the operator) is displayed on the display unit 112. The operating unit 113 includes, for example, a keyboard and a mouse, or various buttons, and inputs the operator's instruction into the apparatus. For example, an instruction to start an examination is input by the operating unit 113.

The imaging control device 111 centrally controls an X-ray imaging process based on imaging protocol information. For example, the imaging control device 111 transmits imaging conditions for the sensor 109 to the sensor 109 to control the drive of the sensor 109. Alternatively, the imaging control device 111 transmits a signal to control a power supply state of the sensor 109 to control the operation of the sensor 109. Moreover, the imaging control device 111 controls image processing on a captured image obtained by the sensor 109. For example, image processing (for example, correction processing, gradation processing, and frequency processing) is performed on the captured image. Image processing is performed with image processing parameters corresponding to imaging protocol information upon imaging. Moreover, the imaging control device 111 performs display control that causes the display unit 112 to display a captured image obtained by the sensor or an image after image processing. Moreover, the imaging control device 111 manages, for example, information indicating the examination progress of an examination order received from the RIS terminal 102 and the imaging progress of each piece of the imaging protocol information. Alternatively, the imaging control device 111 performs communication control such as control that causes images to be output to a storage unit of the PACS and the image quality assurance terminal 103.

The imaging control device 111 is an electronic calculator including, for example, a communication circuit 1111, one or more CPUs 1112, a RAM 1113, an SSD (Solid State Drive) 1114, an I/F (interface) 1115, and an internal bus 1116 that connects them in a manner capable of communication. A plurality of hardware circuits other than the CPU(s) 1112 can be provided to the imaging control device 111.

The communication circuit 1111 connects the sensor 109, the irradiation control unit 110, the communication network 105, and the imaging control device 111 in a manner capable of communication. A communication circuit used for communications in the X-ray imaging apparatus 106 and a communication circuit used for communications via the communication network 105 can be realized separately. The communication circuit 1111 transmits, to the sensor 109 and the irradiation control unit 110, information indicating imaging conditions such as radiographing conditions and irradiation conditions. A captured image obtained by imaging is received from the sensor 109. Information on radiation actually applied is received as performed information from the irradiation control unit 110. Moreover, the communication circuit 1111 receives information on an examination order from the RIS terminal 102. Captured images received by the imaging control device 111, on which image processing have been performed, are transmitted to the image quality assurance terminal 103 and the PACS 104. Moreover, information on an additional imaging instruction is received from the image quality assurance terminal 103.

A computer program that is developed in the RAM 1113 and executed by the CPU 1112 is stored in the SSD 1114.

The I/F 1115 is an interface such as a USB (Universal Serial Bus) or HDMI (registered trademark) (High Definition Multimedia Interface), and connects the display unit 112 and the operating unit 113 to the imaging control device 111.

Various controls such as imaging control, image processing, display control, examination management, and communication control for controlling the drive and operation of the above-mentioned sensor 109 are performed by control in accordance with the above-mentioned computer program. For simplicity, the controls are described below as the operations of an imaging control unit 255, an image processing unit 256, a display control unit 253, an examination management unit 252, and a communication control unit 251. In the embodiment, these units are functional units realized by cooperation between the computer program and the CPU 1112. Moreover, in the imaging control device 111 according to another embodiment, part or all of the units are implemented as hardware by an FPGA by use of configuration data corresponding to the contents of the program.

Moreover, in another embodiment, for example, the display control unit 253 can be a GPU (Graphical Processing Unit) that operates in accordance with control by the CPU 1112. In this case, the display unit 112 can be connected to an output terminal of the GPU.

Moreover, in another embodiment, the imaging control unit 255 can be implemented in a dedicated hardware circuit focusing on real time capability.

The functions of the imaging control device 111 according to the embodiment are described with reference to FIG. 2.

The imaging control device 111 is configured including, for example, an examination acquisition unit 201, an examination storage unit 202, an image acquisition unit 203, an examination information output unit 204, an imaging instruction receiving unit 205, an imaging instruction storage unit 206, a protocol addition determination unit 207, a cancellation instruction unit 208, an additional protocol acquisition unit 209, an image identification unit 210, a re-imaging protocol identification unit 211, a status changing unit 212, a reason changing unit 213, a notification unit 214, a position specification unit 215, and an imaging preparation control unit 216. They can function as, for example, the communication control unit 251, the examination management unit 252, the display control unit 253, a storage unit 254, and the imaging control unit 255 as illustrated in FIG. 2. For example, the communication control unit 251 can include the examination acquisition unit 201, the image acquisition unit 203, the examination information output unit 204, and the imaging instruction receiving unit 205. The examination management unit 252 can include the protocol addition determination unit 207, the cancellation instruction unit 208, the additional protocol acquisition unit 209, the image identification unit 210, the re-imaging protocol identification unit 211, the status changing unit 212, and the reason changing unit 213. The display control unit 253 can include the notification unit 214 and the position specification unit 215. The storage unit 254 can include the examination storage unit 202 and the imaging instruction storage unit 206 as, for example, a storage area in memory. The imaging control unit 255 can include the imaging preparation control unit 216.

The examination acquisition unit 201 acquires examination order information. The examination order information (imaging information) includes information on a patient to be radiographed, and information indicating an imaging content. The examination order information is input from an external system such as the RIS terminal 102. The examination storage unit 202 stores a new examination input from an external system such as the RIS terminal 102 through the examination acquisition unit 201. The storage of a new examination enables the use of the input examination order information even in an offline status. The imaging protocol information forming the examination order information is stored in list form. The image acquisition unit 203 acquires a radiographic image captured by the X-ray imaging apparatus 106. A radiographic image can be input via a network or input via a medium such as a CD-ROM or DVD. The examination information output unit 204 transfers and outputs images and examination information to external apparatuses such as the image quality assurance terminal 103 and the PACS 104.

The imaging instruction receiving unit 205 receives an imaging instruction from an external system such as the image quality assurance terminal 103. The imaging instruction storage unit 206 stores the imaging instruction received by the imaging instruction receiving unit 205. The protocol addition determination unit 207 determines whether imaging protocol information by the imaging instruction input in the imaging instruction receiving unit 205 can be added. The cancellation instruction unit 208 instructs the external system that has input the imaging instruction via the imaging instruction receiving unit 205 about information to the effect that the imaging protocol information could not be added. The additional protocol acquisition unit 209 acquires imaging protocol information to be added to the examination order information based on an imaging instruction input in the imaging instruction receiving unit 205. Imaging protocols to be added include a new protocol to be added and an imaging protocol for re-imaging for an existing imaging protocol. In a case of re-imaging, a process of identifying the existing protocol related to re-imaging is performed. The image identification unit 210 identifies an image targeted for re-imaging based on the imaging instruction received by the imaging instruction receiving unit 205. The re-imaging protocol identification unit 211 identifies re-imaging protocol information based on the reimaging target image identified by the image identification unit 210. The additional protocol acquisition unit 209 includes, for example, the image identification unit 210 and the re-imaging protocol identification unit 211. The status changing unit 212 changes the imaging success/failure status of the captured image to imaging success/failure. The reason changing unit 213 changes the imaging failure reason of the captured image. The notification unit 214 notifies the operator via the display unit 112 that the imaging protocol information has been added. The position specification unit 215 specifies the position in the list of protocols tied to the examination order information to insert the imaging protocol information to be added by the additional protocol acquisition unit 209. The imaging preparation control unit 216 is responsible for control over the imaging ready status of the imaging protocol information.

The flowcharts in FIGS. 5 to 9, 15 to 18, 20 to 25, and 27 to 28 describe examples of processes mainly performed by the imaging control device 111 with such a configuration. The display control unit 253 displays imaging screens illustrated in FIGS. 3, 4, 10 to 14, and 30 to 31, displays windows for notifying an additional imaging instruction in FIGS. 19 and 26, and displays windows for displaying additional protocol candidates in FIGS. 29 and 32. The flows of these processes and the details of the display of the screen or window are described below.

Figure 3:
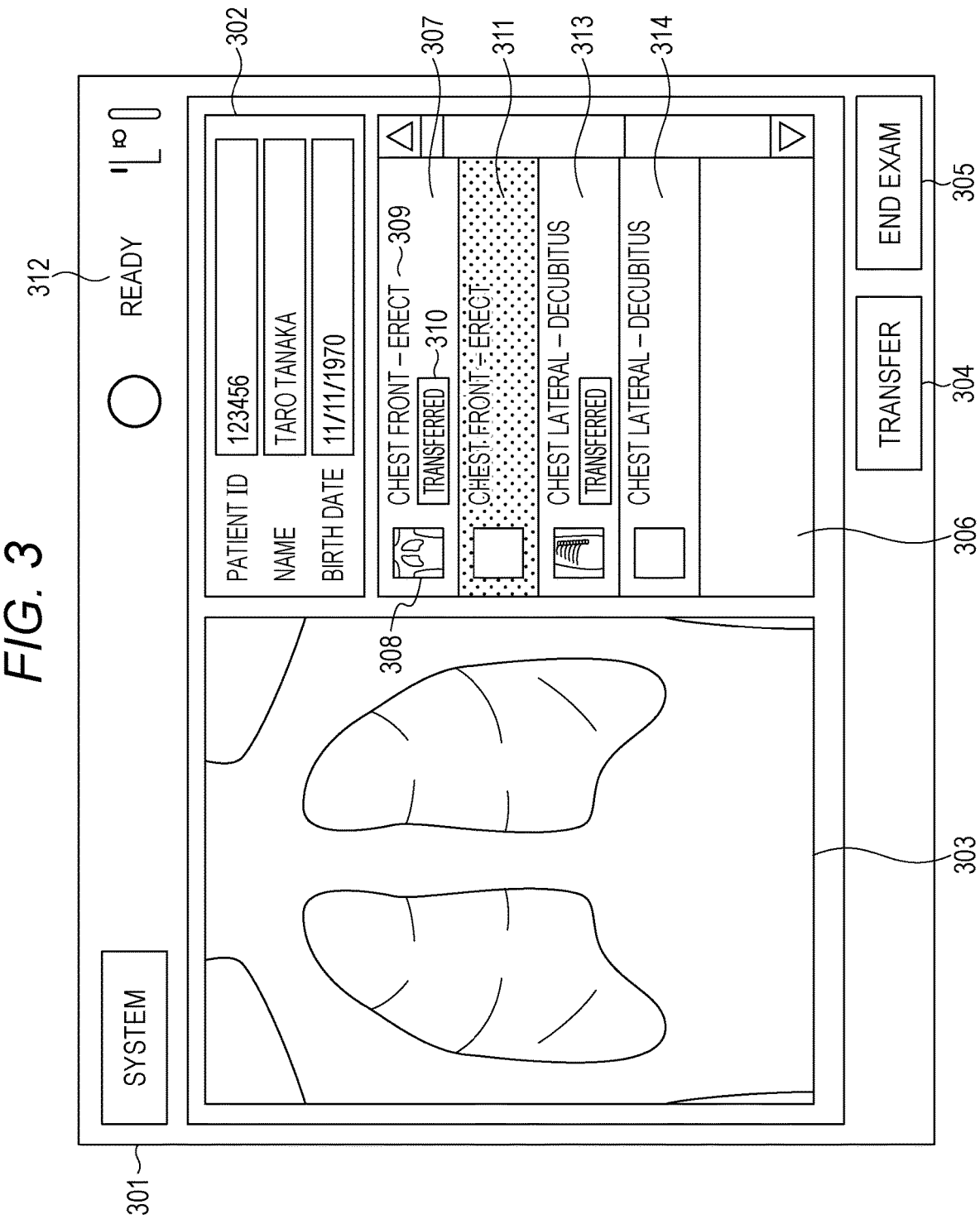
FIG. 3 is a diagram illustrating an example of an imaging screen before the addition of imaging protocol information according to the first to sixth embodiments.
Figure 4:
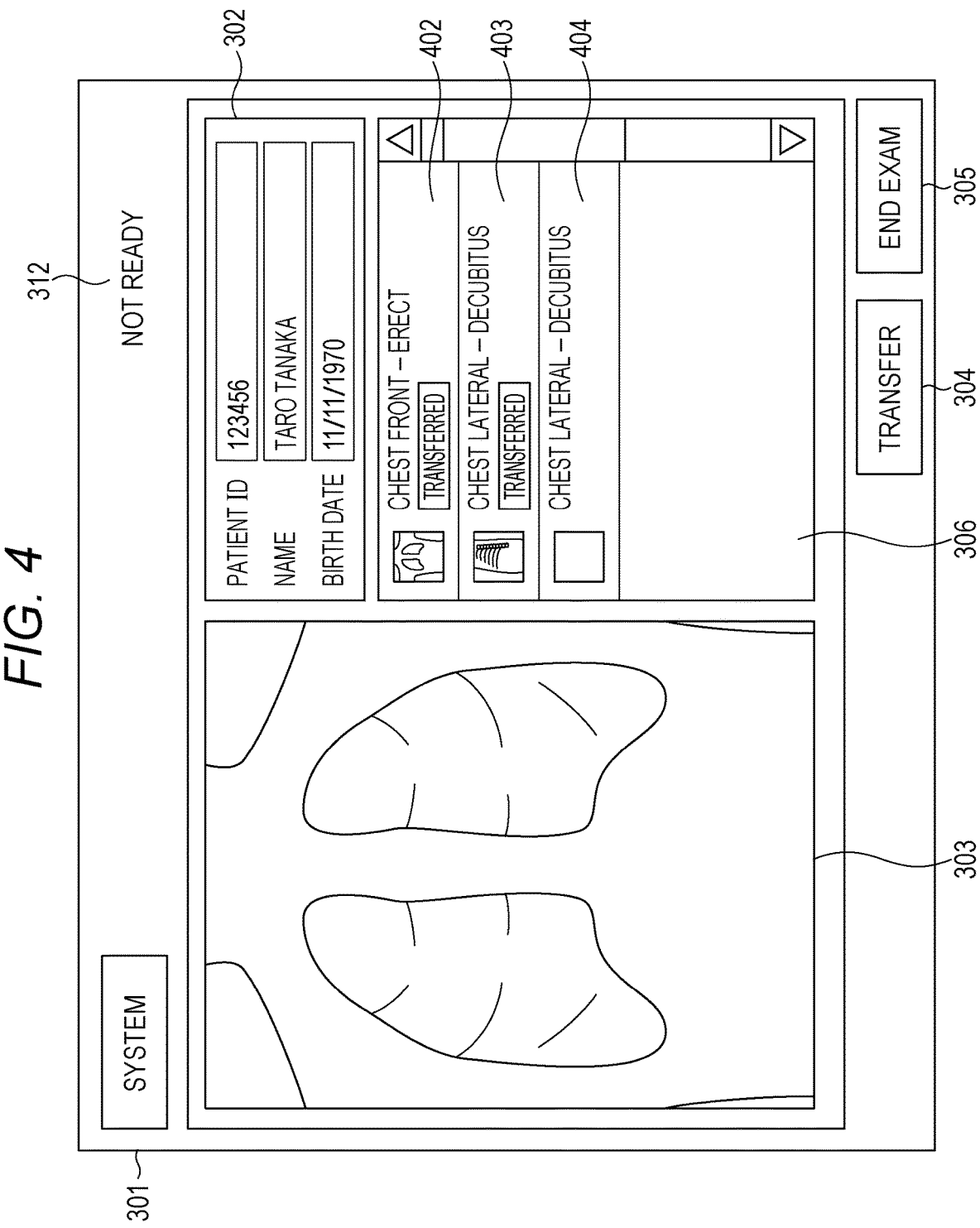
FIG. 4 is a diagram illustrating an example of the imaging screen before the addition of imaging protocol information according to the first to sixth embodiments.

The display control unit 253 displays, on display screens in, for example, FIGS. 3 and 4, imaging information including first imaging protocol information including at least imaging region information, imaging conditions, irradiation conditions, image processing conditions, or output conditions, and examinee information for imaging related to the imaging information. Taking an example of FIG. 3, imaging protocol information 307, 311, 313, 314, and the like correspond to the first imaging protocol information.

Figure 10:
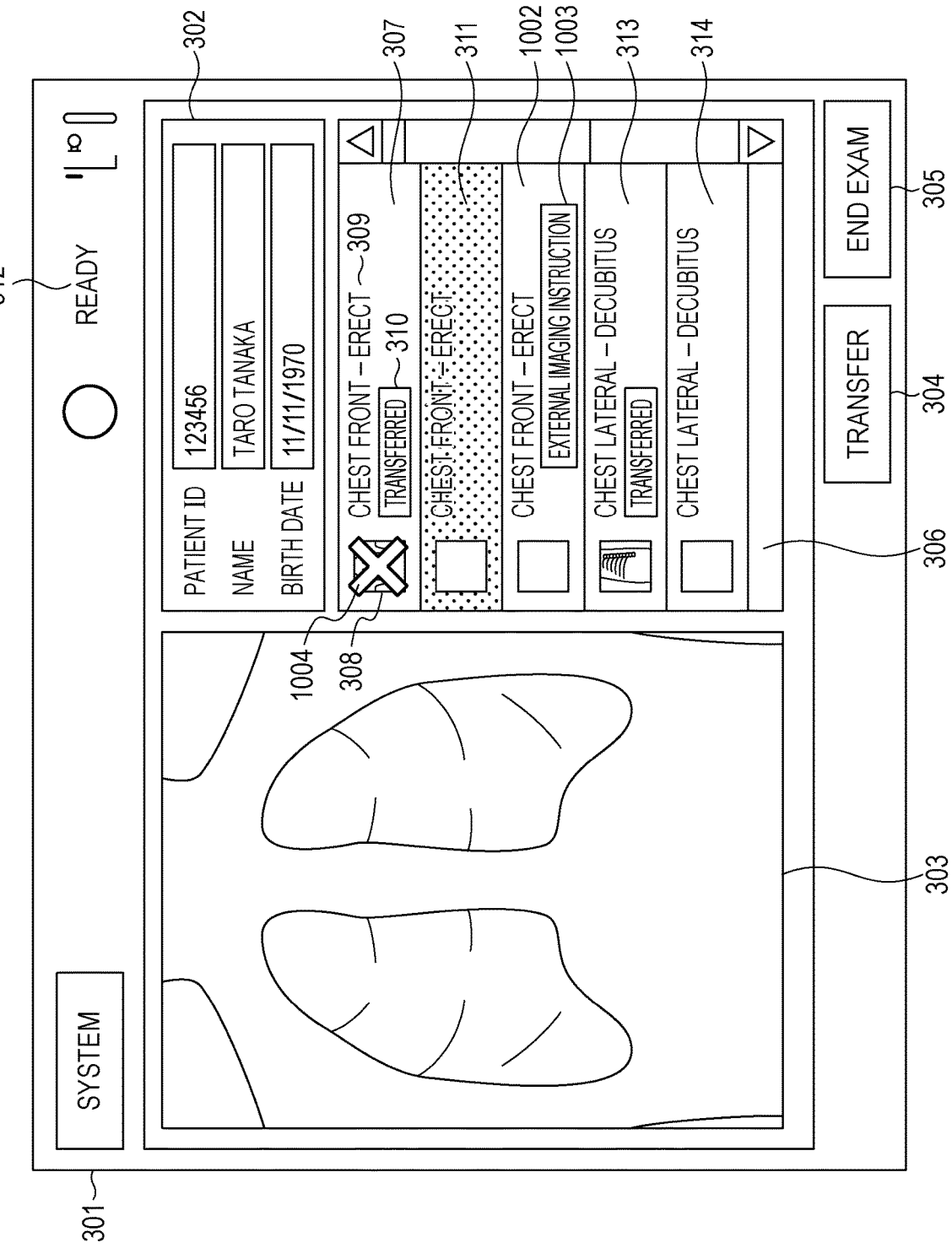
FIG. 10 is a diagram illustrating an example of the imaging screen after the addition of imaging protocol information according to the first to sixth embodiments.

Imaging protocol information for additional imaging (second imaging protocol information), together with the first imaging protocol information included in the imaging information, is displayed as in, for example, imaging protocol information 1002 in FIG. 10. As illustrated in the example of FIG. 10, the display control unit 253 displays the first imaging protocol information 307 in an examination order display area 306 of an imaging screen 301. The second imaging protocol information 1002, in addition to the first imaging protocol information 307, is displayed in the examination order display area 306. Moreover, from another viewpoint, if the second imaging protocol information is acquired while the imaging information including the first imaging protocol information (for example, 307) is being displayed, the second imaging protocol information (1002) is displayed vertically next to the first imaging protocol information. Consequently, the imaging protocol for additional imaging can be handled similarly to the existing imaging protocol. The convenience of a user is improved. In one of the embodiments, the display control unit 253 displays the imaging protocol information included in advance in the examination order information (imaging information), and the imaging protocol information related to additional imaging based on an instruction from the outside, in a manner where the user can distinguish them. Consequently, the user can determine, for example, the imaging order while the user considers where the imaging protocol information originates.

The display control unit 253 performs a process of determining display and placement on where to place additional imaging protocol information based on a relationship with existing imaging protocol information upon the display of the additional imaging protocol information on, for example, the imaging screen 301 in FIG. 3. For example, in a case of list display as in FIG. 3, control over display and placement is achieved by associating each piece of imaging protocol information with a number, displaying them in list form in the order of numbers. In this case, the information indicating display and placement is the number.

There are various forms in the placement of an imaging protocol for additional imaging. For example, based on the concept that a high priority is given to imaging related to existing imaging protocol information, the display control unit 253 is configured to display the imaging protocol information for additional imaging under the existing imaging protocol information as illustrated in, for example, FIG. 13. Assuming, for example, that consecutive numbers indicating display and placement are assigned respectively to pieces of the existing imaging protocol information from 1 to N, a number N+1 is assigned to the imaging protocol information for additional imaging. Alternatively, if additional imaging is suggested for the existing imaging protocol information in the imaging control device 111, a number 9999 can be associated with imaging protocol information based on an instruction from inside the imaging control device 111. Consequently, the imaging protocol information for additional imaging is decided to be always placed and displayed on the bottom of the list except for exceptional circumstances.

Figure 14:
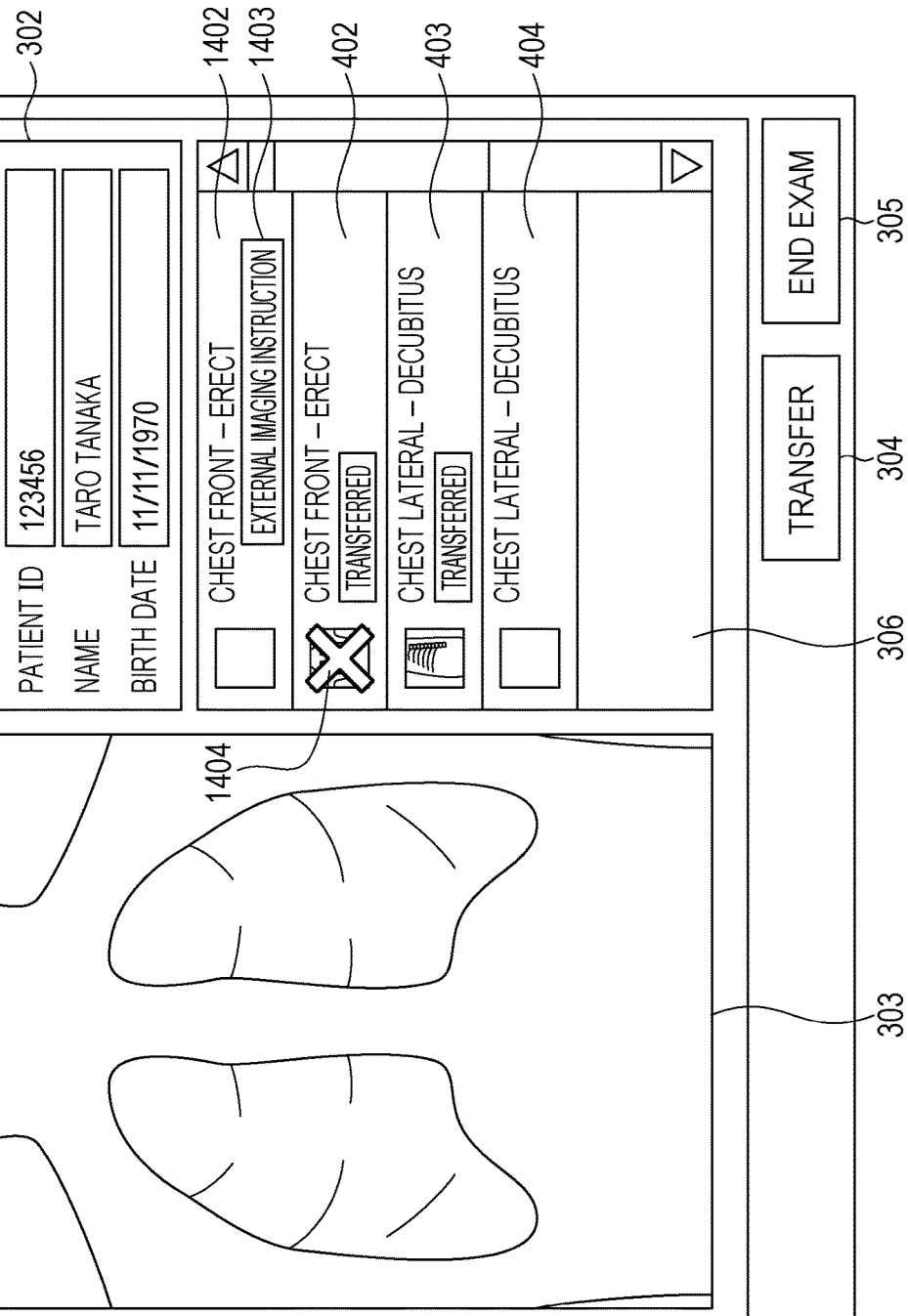
FIG. 14 is a diagram illustrating an example of the imaging screen after the addition of imaging protocol information according to the first to sixth embodiments.

Moreover, for example, the display control unit 253 is configured to display imaging protocol information for additional imaging in such a manner as to be in a higher place in the list than existing imaging protocol as illustrated in FIG. 14 for the purpose of assigning a higher priority to imaging related to the existing imaging protocol information. This is because imaging based on an external instruction can be re-imaging for an image already captured once or additional imaging required upon diagnosis of an examinee who has already undergone radiography. In this case, a number 1 is assigned to imaging protocol information for additional imaging.

Moreover, in terms of such display and placement, display and placement can be determined in such a manner as to keep related imaging protocols together, or can be determined based on information indicating a priority level defined for each piece of imaging protocol information. Moreover, for example, information on an imaging region and the type of sensor used for imaging, which is included in each piece of imaging protocol information, is used to determine display and placement such that, for example, pieces of imaging protocol information whose imaging region and type of sensor are the same—be it existing one or one related to additional imaging—are numbered consecutively.

For example, a case is considered in which in a state where a plurality of pieces of first imaging protocol information included in imaging information are sequentially arranged and displayed, second imaging protocol information for additional imaging corresponds to re-imaging for one of the plurality of pieces of first imaging protocol information. Giving a description taking FIG. 11 as an example, such a case corresponds to that the plurality of the (first) imaging protocol information pieces 307, 311, 313, and 314, and the like are arranged in advance and displayed, and the (second) imaging protocol information 1002 for re-imaging for the imaging protocol information 313 is obtained. In this case, the display control unit 253 determines display and placement in such a manner as to display the (second) imaging protocol information 1002 vertically next to the (first) imaging protocol information 313. Consequently, it is possible to make it easier to understand that the additional imaging protocol is associated with which piece of imaging protocol information among the plurality of pieces of imaging protocol information.

Figure 9:
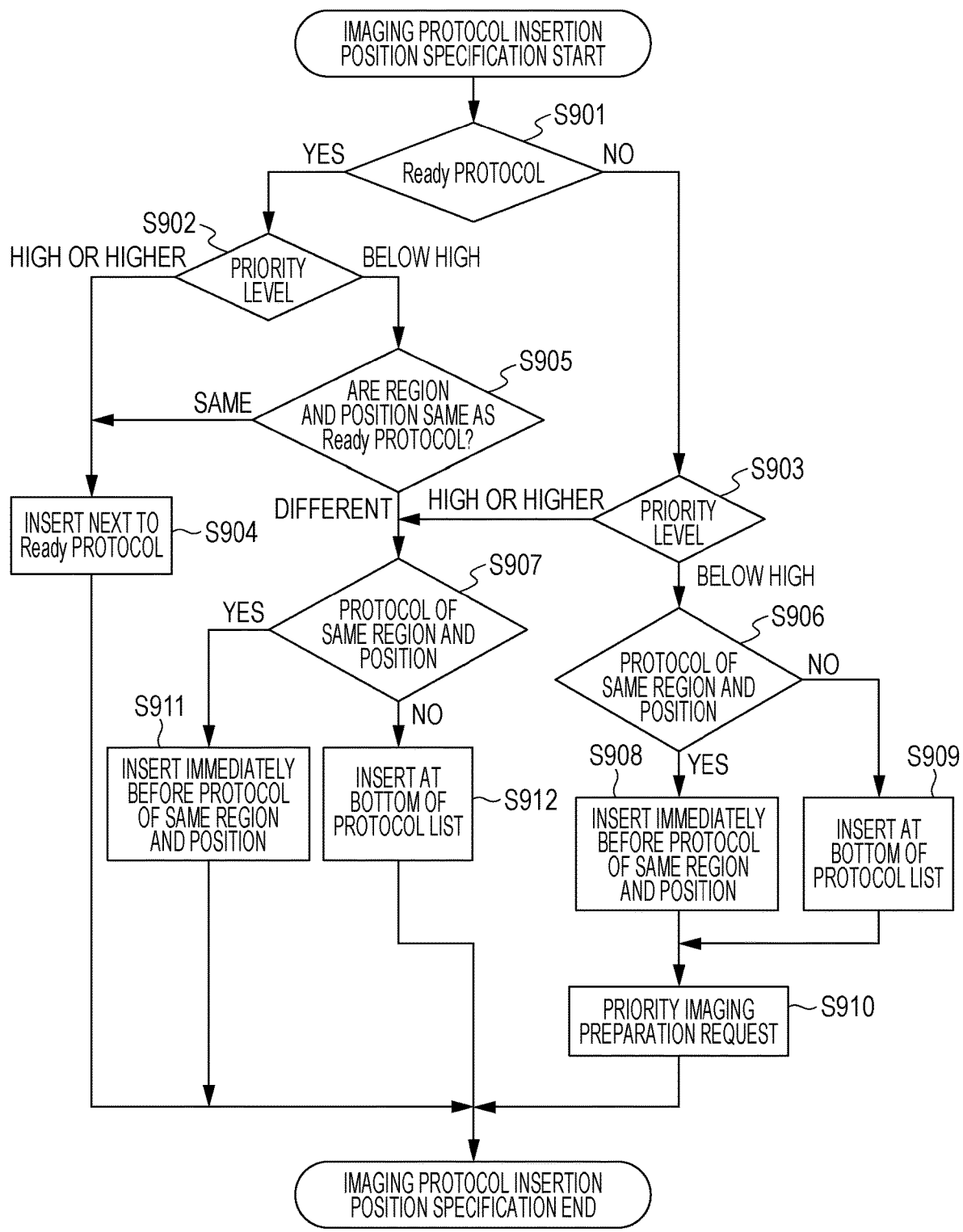
FIG. 9 is a flowchart illustrating an example of a process of specifying an insertion position of additional imaging protocol information according to the first to sixth embodiments.

Moreover, for example, if the external instruction information includes information indicating its imaging priority level, the display control unit 253 controls a display form of the second imaging protocol information related to additional imaging according to the priority level as in, for example, a process illustrated in a flowchart of FIG. 9. Specifically, such a process allows the imaging protocol information for additional imaging to determine its display and placement. In terms of display and placement, the imaging protocol information for additional imaging is determined to be placed in a higher place in the imaging protocol information list displayed in the examination order display area 306 if being assigned a high priority level than if being assigned a low priority level.

Figure 19:
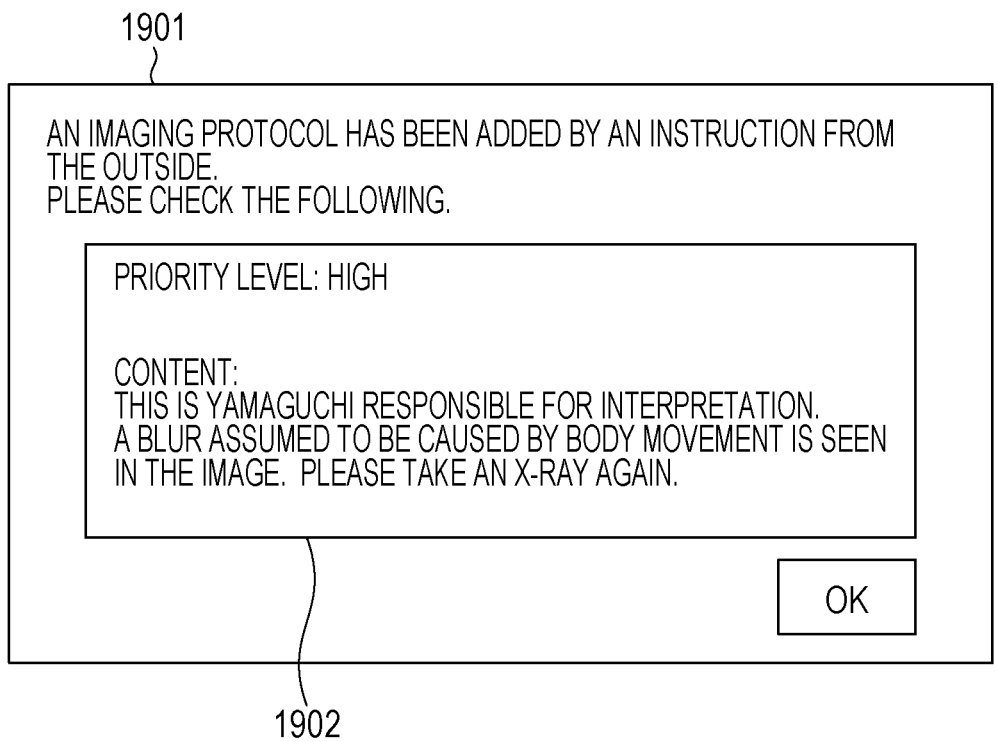
FIG. 19 is a diagram illustrating an example of an imaging protocol information addition notification screen according to the first to third embodiments.

In another embodiment, a display indicating that an additional imaging instruction has been given is controlled according to the priority level. For example, a message indicating the priority level is displayed. Moreover, for example, in a case of a high priority level, it is conceivable that even if imaging protocol information being the next imaging target is determined, such a window as illustrated in FIG. 19, the window indicating that an additional imaging instruction has been given, is displayed superimposed on the imaging screen. On the other hand, in a case of a low priority level, it is conceivable that if imaging protocol information being the next imaging target is determined, such a window as illustrated in FIG. 19, the window indicating that an additional imaging instruction has been given, is displayed superimposed on the imaging screen after imaging related to the imaging protocol information is finished.

The above-mentioned process of determining display and placement can be performed by, for example, the position specification unit 215. Moreover, the process of determining display and placement is described as the function of the position specification unit 215 of the display control unit 253. However, it can be designed as a function of the examination management unit 252.

The above-mentioned priority level information can also be used for other than decision on display and placement. In one of the embodiments, in the case where the above-mentioned priority level is high, even if imaging protocol information being the next imaging target is already specified, instead of this imaging protocol information, (second) imaging protocol for additional imaging is specified as the next imaging target. Such a function corresponds to step S910 of FIG. 9 and FIGS. 14 to 16.

In this case, in response to the specification of the imaging protocol information (in a Ready status) being the original next imaging target, the imaging preparation control unit 216 sets at least the imaging conditions or irradiation conditions included in the imaging protocol information in at least the imaging unit (the sensor 109) or the X-ray tube 107. However, in the embodiment, if imaging on such imaging protocol information being the original next imaging target is unperformed, at least imaging conditions or irradiation conditions included in the (second) imaging protocol information for additional imaging is written over at least the set imaging conditions or irradiation conditions to be set.

Similarly, also in a case where there is no imaging protocol information specified as the next imaging target, if a high priority is assigned to the (second) imaging protocol information for additional imaging, the (second) imaging protocol information for additional imaging can be specified as the next imaging target. Also in this case, the imaging preparation control unit 216 of the imaging control unit 255 is configured to set at least imaging conditions or irradiation conditions included in the (second) imaging protocol information for additional imaging in the imaging unit (the sensor 109) or the X-ray tube 107. Consequently, in terms of additional imaging with a high priority, even the setting of the imaging unit or the irradiation unit can also be automatically performed triggered by an imaging instruction from the outside. Accordingly, efficiency in additional imaging can be improved.

In terms of the level of priority, for example, three levels of priority from one to three are determined in advance. When the priority level is one, an imaging protocol for additional imaging has higher priority than an imaging protocol in the Ready status in terms of the execution of the above-mentioned overwrite setting process. If the priority level is two or three, the above-mentioned overwrite setting is not performed. Moreover, if the priority level is three, it is determined that the priority is low. If the priority level is one or two, it is determined that the priority is high to perform the above-mentioned process of determining display and placement and the above-mentioned message window display control.

If the second imaging protocol information is acquired in a state where the imaging information including the first imaging protocol information is being displayed, the display control unit 253 notifies a user that an additional imaging instruction has been given. Such notification corresponds to, for example, the function of the notification unit 214 of the display control unit 253. Moreover, in another embodiment, the notification unit 214 notifies the user in a form different from display. For example, a predetermined sound is issued from an unillustrated acoustic unit to give notification that there has been an additional imaging instruction. From another viewpoint, the display control unit 253 displays the second imaging protocol information related to additional imaging in a manner distinguishable from the first imaging protocol information included in advance in the examination order information (imaging information).

In the example illustrated in FIG. 10, an identifier 1003 is displayed in a display area of the imaging protocol information 1002 for additional imaging. Accordingly, it is possible to identify that the imaging protocol information 1002 related to the user is related to the additional imaging instruction and is different from the existing imaging protocol information. The display indicating that the additional imaging instruction has been given can be placed in a display area different from the imaging protocol information 1002.

In another embodiment, if an additional imaging instruction has been given, the display control unit 253 or the notification unit 214 displays and superimposes such a window as illustrated in FIG. 19, the window including a message indicating that the additional instruction has been given, on the imaging screen. Consequently, it is notified that the additional imaging instruction has been given. Such a window is displayed, for example, after the imaging protocol information for additional imaging is added to the imaging screen. Consequently, it is possible to prompt the user to check. In such a form, for example, if imaging related to the existing imaging protocol information is all finished, or if imaging related to imaging protocol information on the bottom of the list of imaging protocol information sequentially arranged as in FIG. 10 is finished, the above-mentioned window is displayed. Consequently, it is possible to prevent the reduction of the efficiency of the imaging operation.

Alternatively, when a plurality of pieces of imaging protocol information is displayed, if the above-mentioned window is displayed at a time immediately before the position of the subject for imaging is changed from an erect position to a decubitus position, for example, immediately after the last imaging in the erect position is finished, it is possible to prevent the reduction of the efficiency of the imaging operation.

On the other hand, in another embodiment, the above-mentioned window is displayed before the imaging protocol information for additional imaging is added to the imaging screen and after the information on the additional imaging instruction is received from, for example, the image quality assurance terminal 103. Consequently, a change in display that attracts the user's attention unnecessarily such as that the imaging protocol information is suddenly added is prevented.

Figure 26:
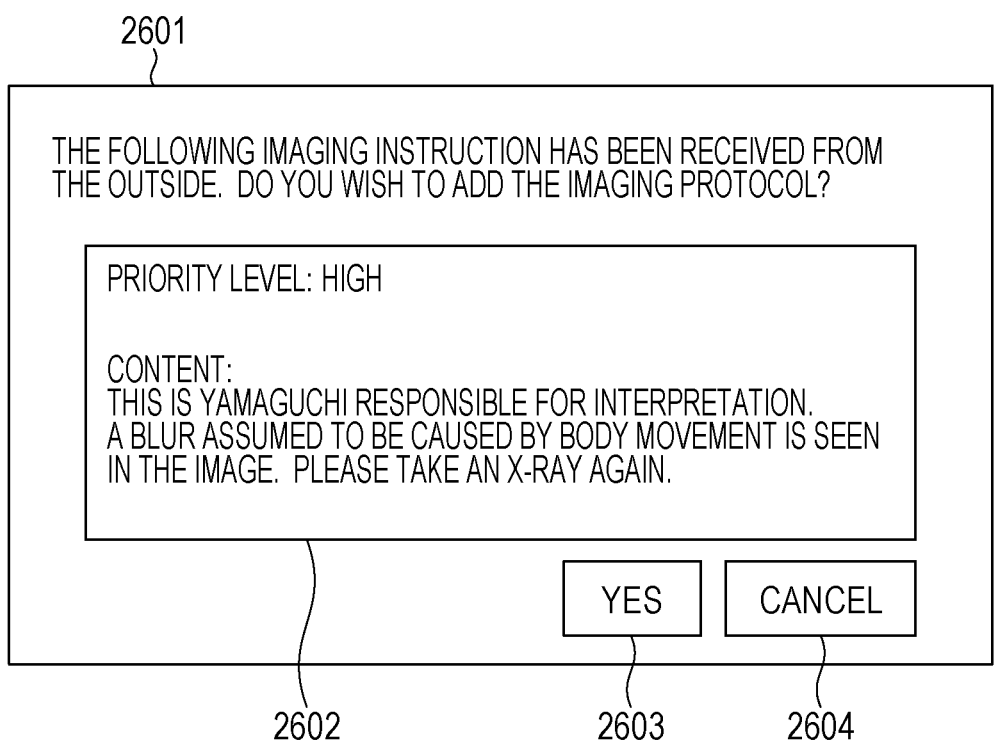
FIG. 26 is diagram illustrating an example of an imaging protocol information addition determination screen according to the fourth embodiment.

Items (an yes button 2603 and a cancel button 2604) for accepting the input of an operation of instructing whether to add an imaging protocol, together with information indicating that an additional imaging instruction has been given, are displayed on the display unit as in FIG. 26. With the input of an operation on such an item, whether to add the imaging protocol information for additional imaging is added is controlled.

The communication control unit 251 outputs information indicating that additional imaging has been accepted through the communication circuit 1111 in response to the acceptance of the input of the operation of instructing the addition of the imaging protocol, for example, at the press of the yes button 2603. Moreover, the communication control unit 251 outputs information indicating that the additional imaging has been refused in response to the acceptance of the input of the operation instructing the non-addition of the imaging protocol, for example, at the press of the cancel button 2604. The output destination can be set to, for example, the image quality assurance terminal 103 being the transmission source that has transmitted the additional imaging instruction. The image quality assurance terminal 103 receives such information. Accordingly, it is convenient since the user of the image quality assurance terminal 103 can find information on whether imaging has been reserved as instructed by the user (whether the imaging protocol information has been added). For example, if the yes button 2603 is pressed, the imaging protocol information for additional imaging is displayed on the imaging screen 301, and a captured image is obtained, the communication control unit 251 transmits the captured image to the image quality assurance terminal 103 by an immediate transfer function without waiting for the end of the examination. Moreover, if the cancel button 2604 is pressed, a text box for inputting a reason for the cancellation or refusal is displayed in the window. Information on the reason for the cancellation or refusal, together with the information indicating that additional imaging has been refused, is output to the outside. Consequently, the reason for the refusal on the image quality assurance terminal 103 side can be checked and can also be kept as a record.

Various ways are conceivable to obtain imaging protocol information for additional imaging: (1) receive it from the image quality assurance terminal 103, (2) specify it with the input of an operation from the operating unit 113 of the imaging control device 111, and (3) the examination management unit 252 of the imaging control device 111 generates it based on part of information received from the image quality assurance terminal 103. In the case (1), the additional protocol acquisition unit 209 of the examination management unit 252 acquires information received through the communication circuit 1111 as the imaging protocol information. In the case (2), the display control unit 253 displays, for example, windows illustrated in FIGS. 29 and 31 to allow the acceptance of the input of an operation for specifying imaging protocol information. The additional protocol acquisition unit 209 specifies imaging protocol information in accordance with the input of such an operation as the imaging protocol for additional imaging.

A process in the case (3) is described below. For example, the following cases are conceivable: a case (i) where the communication circuit 1111 receives instruction information including information indicating identification information of a captured image from the image quality assurance terminal 103; and a case (ii) where instruction information including an examination ID and part of information on various conditions that is required to be included in the imaging protocol information are received from the image quality assurance terminal 103.

The case (i) is used mainly for the purpose of re-imaging. The image identification unit 210 of the additional protocol acquisition unit 209 identifies a captured image corresponding to the received identification information. The re-imaging protocol identification unit 211 identifies imaging protocol information associated with the captured image. The additional protocol acquisition unit 209 generates new imaging protocol information including various conditions included in such imaging protocol information and new identification information as the imaging protocol information for additional imaging. The generated imaging protocol is associated with examination order information corresponding to the received identification information of the captured image. As describe above, if the instruction information received from the image quality assurance terminal 103 includes identification information of an image, the additional protocol acquisition unit 209 acquires the second imaging protocol information based on imaging protocol information of the image identified by the identification information.

The case (ii) is used for additional imaging including re-imaging. The additional protocol acquisition unit 209 identifies examination order information based on identification information of the received examination order information (imaging information). A partial match search is made targeting list information of specifiable imaging protocol information stored in advance in the SSD 1114 based on the received part of the information on the various conditions. If imaging protocol information can be uniquely identified, imaging protocol information for additional imaging is generated from the identified imaging protocol information. If imaging protocol information cannot be uniquely identified, a plurality of imaging protocols whose similarity is higher than a threshold, which has been found by the partial match search, is displayed as candidates. For example, a selection is made by the input of an operation on the operating unit 113 to specify one of the candidates. The imaging protocol information selected in this manner is associated as the imaging protocol information for additional imaging with the examination order information identified by the above-mentioned process.

As described in (i) and (ii), the additional protocol acquisition unit 209 acquires the (second) imaging protocol information for additional imaging based on the instruction information received from the image quality assurance terminal 103. Consequently, the imaging protocol information for additional imaging can be efficiently obtained. It is possible to reduce the burden of an operation on the operator and also reduce the risk of generating incorrect imaging protocol information.

Moreover, examination order information (imaging information) that is required to be associated with (second) imaging protocol information for additional imaging is identified based on identification information of an image or identification information of the examination order information (imaging information) included in instruction information received from the image quality assurance terminal 103. Consequently, the imaging protocol information for additional imaging can be associated with appropriate examination order information (imaging information). Accordingly, the burden of an operation on the operator can be reduced.

As described above, additional imaging includes re-imaging for given imaging and additional imaging not limited to re-imaging. In a case of re-imaging, re-imaging is associated with original imaging. Accordingly, it is possible to, for example, specify an image related to the original imaging as a failure and reuse the original imaging conditions. Hence, in one of the embodiments, the examination management unit 252 determines whether the (second) imaging protocol information for additional imaging is the imaging protocol information related to re-imaging for the existing (first) imaging protocol information. In such a determination process, for example, in a case (i) where the instruction information from the image quality assurance terminal 103 includes identification information of an image, it is determined to be re-imaging for imaging corresponding to the image. Alternatively, in a case (ii) where when instruction information of additional imaging is received from the image quality assurance terminal, the display control unit 253 displays, on the display unit 112, a button for accepting the input of an operation indicating re-imaging or not and a list of candidates for the original imaging protocol information in the case of re-imaging. If such a button has been pressed by the input of an operation, and the original imaging protocol information has been selected from the candidate list, the examination management unit 252 determines that re-imaging for the selected imaging protocol information is instructed.

For example, imaging (re-imaging) based on the (second) imaging protocol for additional imaging determined to be re-imaging is performed to obtain a captured image. If the image is not determined to be failed and is output to the image quality assurance terminal 103, a captured image related to the original imaging protocol information becomes unnecessary. Hence, the examination management unit 252 specifies the captured image as a failure. In this case, flag information indicating a failure is associated with the captured image. Moreover, in this case, a display indicating that the captured image corresponding to the original (first) imaging protocol information is failed is displayed to present the user that the captured image is specified as a failure. An identifier 1004 of FIG. 10 is superimposed and displayed within the area of the imaging protocol information 307, for example, on a thumbnail displayed in a thumbnail display area 308. Such a process of specifying and displaying a failure may not be performed according to the setting.

Figure 28:
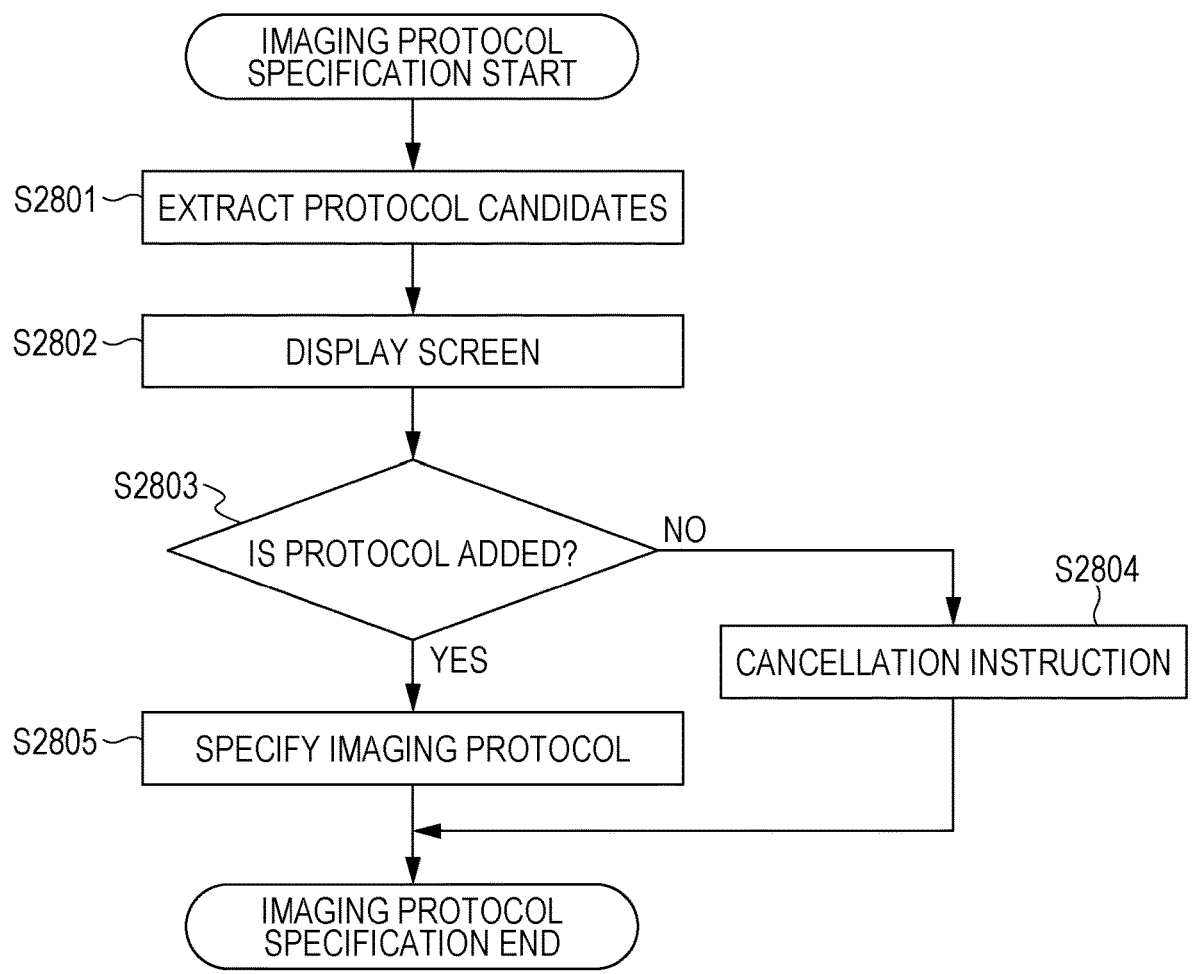
FIG. 28 is a flowchart illustrating an example of an imaging protocol information specification process according to the fifth and sixth embodiments.
Figure 29:
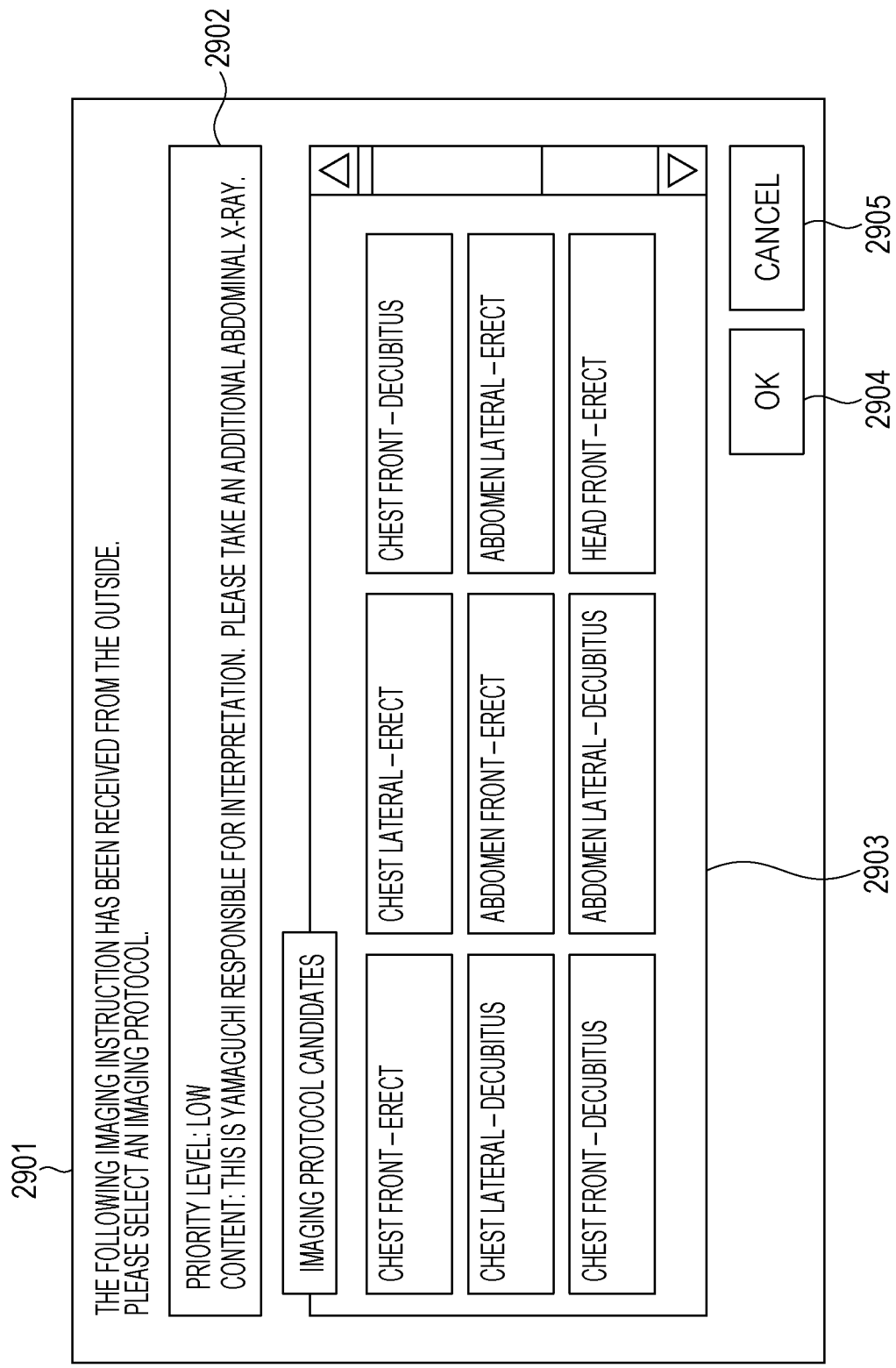
FIG. 29 is a diagram illustrating an example of an imaging protocol information selection screen according to the fifth embodiment.

The display of the imaging screens illustrated in FIGS. 3, 4, 10 to 14, and 30 to 31, the display of the windows for notifying an additional imaging instruction in FIGS. 19 and 26, the display of the windows for displaying candidates for the additional protocol in FIGS. 29 and 32 are described in detail. In addition, the flows of processes described in the flowcharts of FIGS. 5 to 9, 15 to 18, 20 to 25, and 27 to 28, are described.

FIGS. 3 and 4 illustrate examples of the imaging screen displayed on the display unit 112. FIGS. 3 and 4 each illustrate the imaging screen 301 before the addition of imaging protocol information by an imaging instruction from an external system.

In FIGS. 3 and 4, an examinee information display area 302 for displaying examinee information, a preview image display area 303 for displaying a captured image, a transfer button 304 for instructing the transfer of a captured image to the outside, an end exam button 305 for instructing the end of an examination, and an examination order display area 306 for showing information of examination order information in progress are provided. The examination order display area 306 is provided with a plurality of pieces of imaging protocol information including the imaging protocol information 307.

The imaging protocol information 307 is provided with the thumbnail display area 308 for displaying a thumbnail of a captured image, a region display area 309 for displaying the name of an imaging region, and a transfer status display area 310 for displaying whether the captured image has already been transferred to the outside. Moreover, the imaging protocol information 307 also indicates various statuses such as a preview status and an imaging ready status.

In addition, a sensor status display area 312 showing the status of the sensor related to imaging protocol information in progress is also provided to the screens illustrated in FIGS. 3 and 4. In FIG. 3, the imaging protocol information 311 is in the imaging ready status. Accordingly, the imaging ready status and the imaging position of the imaging protocol information 311 are shown in the sensor status display area 312 in FIG. 3. On the other hand, there is no imaging protocol information in the imaging ready status in FIG. 4. Accordingly, information to the effect that no imaging protocol information is in the imaging ready status is displayed in the sensor status display area 312 in FIG. 4.

In the screens illustrated in FIGS. 3 and 4, the status is indicated by characters. However, the status can be indicated by a GUI, for example, by changing the color of the button, or animation display.

A specific example of the flow of processing according to the first embodiment is cited.

A series of procedures from the start to the end of an examination is described with reference to FIG. 5. Such processing is executed mainly by, for example, the imaging control device 111, the sensor 109, and the X-ray tube 107.

First, in step S501, the communication circuit 1111 allows the input of examination order information acquired from the RIS terminal 102 into the examination acquisition unit 201. The input examination order information is stored in the examination storage unit 202. The examination order information and information indicating the progress of each piece of imaging protocol information included in the examination order information are associated and stored in the storage unit 254. Consequently, the examination management unit 252 manages the progress of the examination. Next, execution proceeds to step S502.

In step S502, the examination management unit 252 sets the progress of the examination order information to an examination started status. Consequently, the examination is started to display the imaging screen 301 on the display unit 112. The display control unit 253 displays, on the display unit 112, the examination order information (imaging information) including the first imaging protocol information including at least imaging region information, imaging conditions, irradiation conditions, image processing condition, or output conditions, and examinee information of imaging related to the imaging information.

Next, execution proceeds to step S503.

In step S503, the imaging preparation control unit 216 changes unimaged imaging protocol information to the imaging ready status via the operator's operation of the operating unit 113. The change process can be control in which the imaging preparation control unit 216 automatically changes unimaged imaging protocol information on the top of an imaging protocol information list to the imaging ready status not via the operator's operation. A specific flow of processing of the imaging preparation control unit 216 is described in FIG. 16. Next, execution proceeds to step S504.

In step S504, at the press of an unillustrated irradiation button by the operator, the X-ray tube (irradiation unit) 107 of the X-ray imaging apparatus 106 irradiates a subject with X-rays, and also the sensor 109 detects X-rays that has passed through the subject. The resultant captured image is input into the imaging control device 111 via the image acquisition unit 203. In the imaging control device 111, image processing such as correction processing, gradation processing, and frequency processing is performed on the captured image by use of image processing parameters tied to the imaging protocol information. An identifier that uniquely identifies the image is assigned to the captured image. The captured image is further tied to the imaging protocol information used for imaging to be stored in the examination storage unit 202. The captured image is displayed in the preview image display area 303. Moreover, a thumbnail of the captured image is displayed in the thumbnail display area 308 of the imaging protocol information used for imaging. When imaging corresponding to given imaging protocol information is finished, the examination management unit 252 changes the progress of the imaging protocol to an imaged status. Next, execution proceeds to step S505.

In step S505, at the press of the transfer button 304 via the operation of the operating unit 113, the examination information output unit 204 transfers the captured image to the outside. The captured image is transferred to the image quality assurance terminal 103. At this point in time, the image identifier, together with the captured image, is transferred. The transfer process can be control in which the imaging control device 111 automatically transfers the captured image not via the operator's operation after the processing of step S504 is completed.

With the above-mentioned processing, the communication circuit 1111 outputs, to the image quality assurance terminal 103, the captured image obtained based on the first imaging protocol information included in the examination order information (imaging information) by the control by the communication control unit 251. Next, execution proceeds to step S506.

In step S506, the examination management unit 252 determines whether imaging based on the examination order information has all been completed, according to the press or non-press of the end exam button 305. The determination is made checking whether the imaging protocol information in the examination order information is in the imaged status. If the examination is not completed, execution returns to step S503. If the examination is completed, execution proceeds to step S507.

In step S507, the examination management unit 252 changes the progress of the examination order information acquired in step S501 to a complete status to end the processing.

The flow of an image quality assurance process in the image quality assurance terminal 103 is described with reference to FIG. 6. The processing of all of steps S601 to S605 is executed mainly by the image quality assurance terminal 103.

First, in step S601, the image quality assurance terminal 103 stands by until a captured image is transferred from the imaging control device 111. When a captured image has been transferred by the processing of step S505 in FIG. 5, execution exceeds to step S602.

In step S602, information including the captured image transferred from the imaging control device 111 is received. In addition to the captured image, at least part of information on the captured image and examination order information including examinee information of the captured image can be received. The image quality assurance terminal 103 displays the received captured image on the terminal display unit 1032. Next, execution proceeds to step S603.

In step S603, the terminal CPU 1035 of the image quality assurance terminal 103 determines whether the captured image is of quality suitable for diagnosis based on the input of an operation by an examination technologist who observes the captured image displayed on the image quality assurance terminal 103. If it is determined not to be suitable for diagnosis, execution proceeds to step S604. If it is determined to be suitable for diagnosis, execution proceeds to step S605.

In step S604, the terminal communication circuit 1034 of the image quality assurance terminal 103 instructs the imaging control device 111 on re-imaging to obtain a captured image suitable for diagnosis. Specifically, an imaging instruction is transmitted to the imaging control device 111 via the operation of the image quality assurance terminal 103. The imaging instruction includes an image identifier incidental to the captured image received in step S602, an imaging instruction reason input via an operation on the image quality assurance terminal 103, and the priority level of the instruction. The priority level can be designated as, for example, urgent, high, middle, and low. In addition, the imaging instruction can include identification information of the examination order information of the captured image, and at least imaging region information, imaging conditions, irradiation conditions, image processing conditions, or output conditions, instead of, or in addition to, the identification information of the captured image.

With the above-mentioned processing, the terminal communication circuit 1034 transmits the instruction information including at least imaging region information, imaging conditions, irradiation conditions, image processing conditions, or output conditions, and the identification information of the examination order information of the captured image to the imaging apparatus in response to the input of the operation of instructing additional imaging. Alternatively, the terminal communication circuit 1134 transmits the instruction information including the identification information of the captured image to the imaging apparatus in response to the input of the operation of instructing additional imaging. Naturally, the above-mentioned conditions, the identification information of the examination order information, and the identification information of the image can be transmitted. Execution then returns to step S601.

In step S605, the terminal communication circuit 1034 of the image quality assurance terminal 103 transfers the captured image received in step S602 to the PACS 104 via the operation of the image quality assurance terminal 103. The transferred captured image is saved in the PACS 104. Execution then returns to step S601.

The flow of the process of adding imaging protocol information based on an imaging instruction received by the imaging control device 111 during examination is described with reference to FIG. 7. Such a process is executed mainly by the imaging control device 111. Since the examination is in progress, it is the flow of processing in a situation from the start to the end of the examination, that is, from steps S502 to S507, in FIG. 5.

First, in step S701, the imaging control device 111 stands by until receiving an imaging instruction from the image quality assurance terminal 103. When an imaging instruction has been transmitted by the processing of step S604 in FIG. 6, execution proceeds to step S702.

Figure 6:
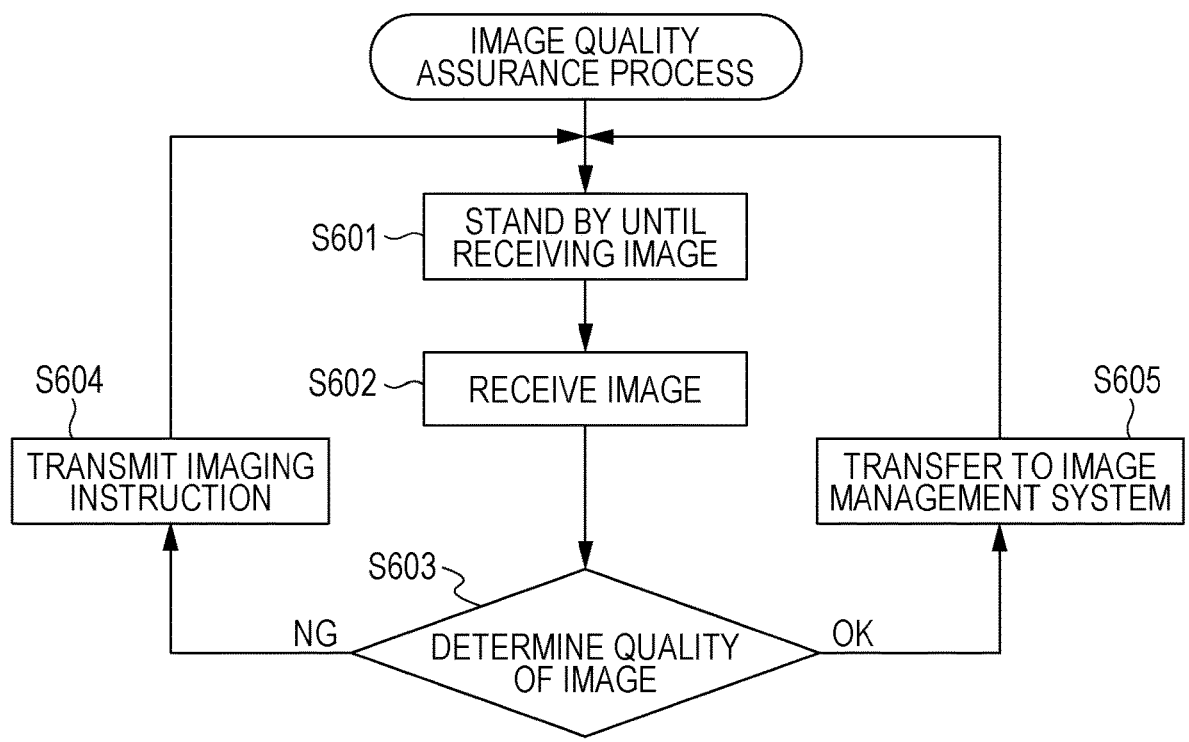
FIG. 6 is a flowchart illustrating an example of an image quality assurance process according to the first to sixth embodiments.

In step S702, the imaging instruction receiving unit 205 receives the imaging instruction transmitted in step S604 in FIG. 6. The received imaging instruction is stored in the imaging instruction storage unit 206. Next, execution proceeds to step S703.

In step S703, the protocol addition determination unit 207 determines whether the number of pieces of imaging protocol information stored in the examination storage unit 202 has reached a specified upper limit. If it has been determined that the number of pieces of imaging protocol information has reached the upper limit, execution proceeds to step S704. If it has been determined that the number of pieces of imaging protocol information has not reached the upper limit, execution proceeds to step S705.

In step S704, the cancellation instruction unit 208 transmits, to the image quality assurance terminal 103, a cancellation instruction indicating that imaging based on the imaging instruction of step S604 in FIG. 6 has been canceled. Execution then returns to step S701.

In step S705, the protocol addition determination unit 207 determines whether the number of radiation doses stored in the examination storage unit 202 has reached a specified upper limit. If it has been determined that the number of radiation doses has reached the upper limit, execution proceeds to step S704. If it has been determined that the number of radiation doses has not reached the upper limit, execution proceeds to step S706.

In step S706, the additional protocol acquisition unit 209 acquires imaging protocol information for additional imaging based on an imaging instruction from the image quality assurance terminal 103 that has received the captured image output in step S505.

Figure 8:
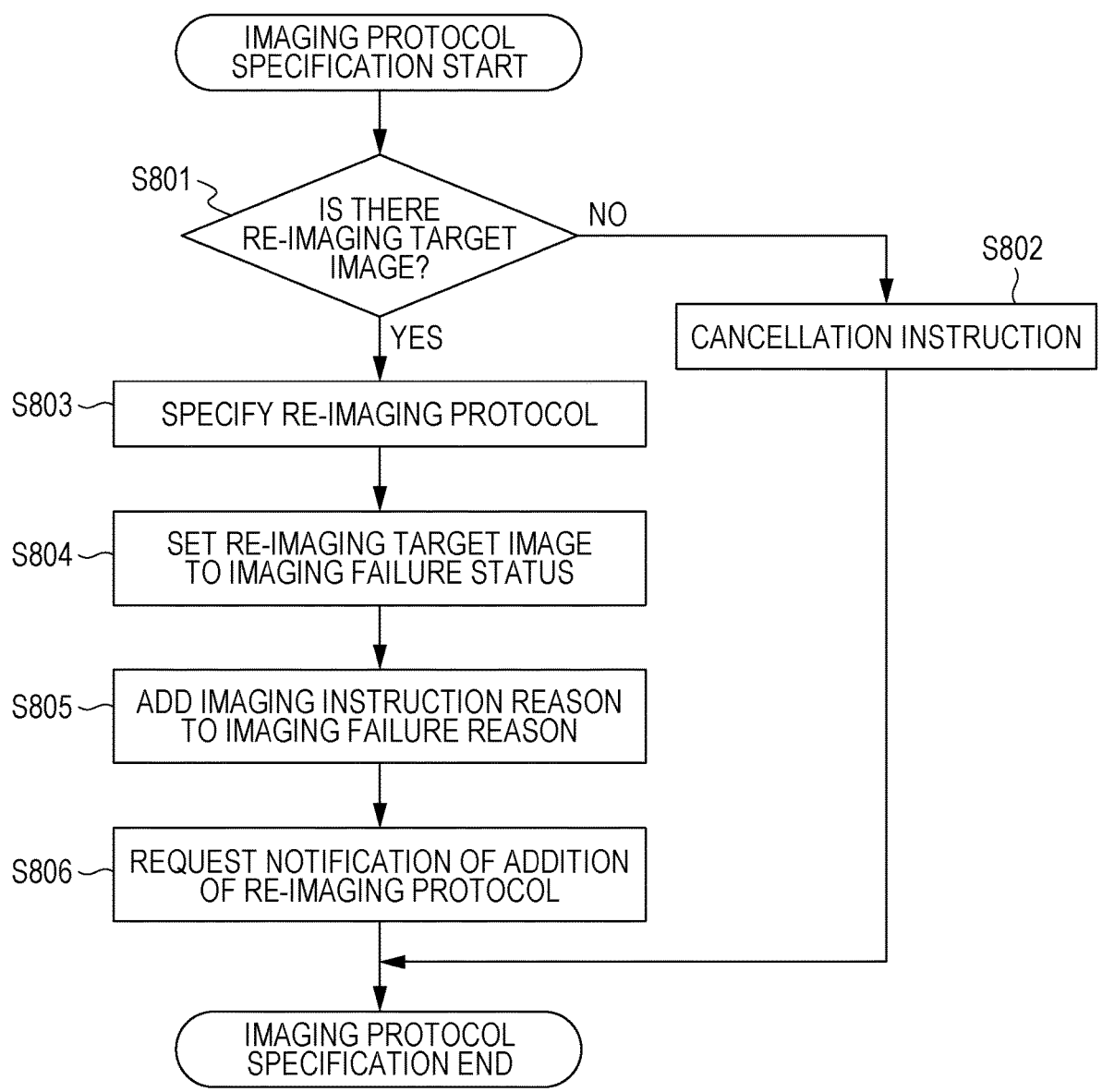
FIG. 8 is a flowchart illustrating an example of an imaging protocol information specification process according to the first embodiment.

A specific processing flow of step S706 is described in accordance with the flowchart of FIG. 8. Such processing is executed mainly by the imaging control device 111.

First, in step S801, the image identification unit 210 identifies a captured image targeted for re-imaging. Specifically, the imaging instruction stored in the imaging instruction storage unit 206 includes the image identifier (see the processing of step S604 in FIG. 6). Captured images stored in the examination storage unit 202 are searched based on the image identifier for a captured image with the same image identifier. If an applicable captured image cannot be found, execution proceeds to step S802. If an applicable captured image can be found, the found captured image is identified as a re-imaging target, and then execution proceeds to step S803.

Figure 7:
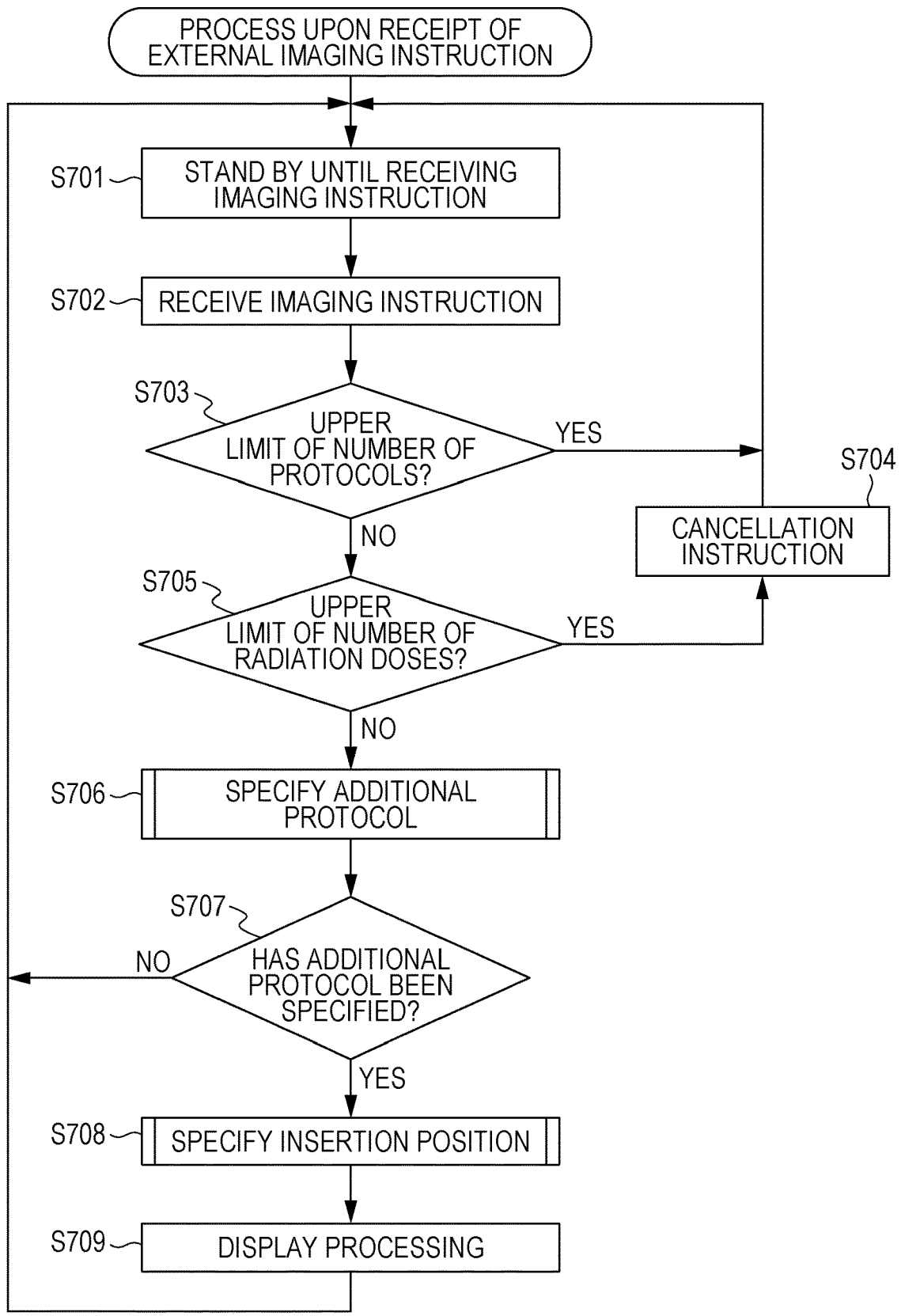
FIG. 7 is a flowchart illustrating an example of a process upon receipt of an external imaging instruction according to the first embodiment.

The processing of step S802 is the same as that of step S704 in FIG. 7; therefore, its description is omitted. Next, execution proceeds to step S707 in FIG. 7.

In step S803, the re-imaging protocol identification unit 211 identifies imaging protocol information used for re-imaging. Specifically, the same imaging protocol information as imaging protocol information tied to the captured image identified by the image identification unit 210 in step S801 is identified as for re-imaging. Next, execution proceeds to step S804.

In step S804, the status changing unit 212 changes an imaging success/failure status incidental to the captured image identified by the image identification unit 210 in step S801 to imaging failure. Next, execution proceeds to step S805.

In step S805, the reason changing unit 213 performs a process of adding an imaging instruction reason included in the imaging instruction stored in the imaging instruction storage unit 206 to an imaging failure reason incidental to the captured image identified by the image identification unit 210 in step S801. Next, execution proceeds to step S806.

In step S806, the notification unit 214 is requested for a notification. Next, execution proceeds to step S707 in FIG. 7.

In step S707, if imaging protocol information to be added has been specified by the processing of step S706 by the additional protocol acquisition unit 209, execution proceeds to step S708. If imaging protocol information to be added has not been specified, execution returns to step S701.

In step S708, the position specification unit 215 specifies where in the list of imaging protocol information included in the examination order information the imaging protocol information is inserted.

A specific processing flow of step S708 is described in accordance with the flowchart of FIG. 9. Such processing is executed mainly by the imaging control device 111.

First, in step S901, it is determined whether the imaging protocol information included in the examination order information includes imaging protocol information in the imaging ready status. If there is imaging protocol information in the imaging ready status, execution proceeds to step S902. If not, execution proceeds to step S903.

In step S902, it is determined whether the priority level included in the imaging instruction stored in the imaging instruction storage unit 206 is equal to or more than a specified threshold. If the priority level is equal to or more than the specified threshold, execution proceeds to step S904. If the priority level is less than the specified threshold, execution proceeds to step S905.

In step S903, a similar determination to that of step S902 is made. If the priority level is equal to or more than the specified threshold, execution proceeds to step S906. If the priority level is less than the specified threshold, execution proceeds to step S907.

In step S904, the imaging protocol information acquired by the additional protocol acquisition unit 209 is inserted at a position after the imaging protocol information that is currently in the imaging ready status among the imaging protocol information included in the examination order information. Next, execution proceeds to step S709 in FIG. 7.

In step S905, the imaging region and position incidental to the imaging protocol information that is currently in the imaging ready status is determined whether to be the same as the imaging region and position incidental to the imaging protocol information acquired by the additional protocol acquisition unit 209. If it is determined to be the same, execution proceeds to step S904. If it is determined to be different, execution proceeds to step S907.

In step S906, it is determined whether there is unimaged imaging protocol information with the same imaging region and position as those incidental to the imaging protocol information specified by the additional protocol acquisition unit 209 among the imaging protocol information included in the examination order information. If there is the same imaging protocol information, execution proceeds to step S908. If not, execution proceeds to step S909.

In step S907, a similar determination to that of step S906 is made. If there is the same imaging protocol information, execution proceeds to step S911. If not, execution proceeds to step S912.

In step S908, the unimaged imaging protocol information with the same imaging region and position as those incidental to the imaging protocol information specified by the additional protocol acquisition unit 209 is searched for from the top of the list of the imaging protocol information included in the examination order information. The imaging protocol information specified by the additional protocol acquisition unit 209 is inserted at a position immediately before imaging protocol information that matches first. Next, execution proceeds to step S910.

In step S909, the imaging protocol information specified by the additional protocol acquisition unit 209 is inserted at the top of the list of the imaging protocol information included in the examination order information. Next, execution proceeds to step S910.

In step S910, the imaging preparation control unit 216 is requested for a priority imaging preparation to preferentially change the imaging protocol information inserted in step S908 or S909 to the imaging ready status. Next, execution proceeds to step S709 in FIG. 7.

In step S911, similar processing to that of step S908 is performed. Next, execution proceeds to step S709 in FIG. 7.

In step S912, the imaging protocol information specified by the additional protocol acquisition unit 209 is inserted at the bottom of the list of the imaging protocol information included in the examination order information. Next, execution proceeds to step S709 in FIG. 7.

In step S709, the display of the imaging screen displayed on the display unit 112 is updated. Consequently, the (second) imaging protocol information for additional imaging, together with the first imaging protocol information included in the imaging information, is displayed. The insertion position of the imaging protocol information for additional imaging is different depending on the determination by the position specification unit 215 in step S708. FIGS. 10, 11, 12, 13, and 14 each illustrate an insertion position on the imaging screen. After updating the display, execution returns to step S701.

FIG. 10 illustrates an example of the imaging screen after the addition of imaging protocol information by an external imaging instruction, the imaging screen being displayed on the display unit 112. The flow until the screen of FIG. 10 is displayed is specifically described. First, what is displayed on the display unit 112 is assumed to be the imaging screen 301 of FIG. 3. In step S505 in FIG. 5, the image captured on the imaging protocol information 307 of FIG. 3 is assumed to be transferred to the image quality assurance terminal 103 at the press of the transfer button 304 via the operation of the operating unit 113. It is assumed that the image displayed on the image quality assurance terminal 103 in step S603 in FIG. 6 is then determined not to be of quality suitable for diagnosis, and an imaging instruction is transmitted in step S604. At this point in time, it is assumed that an image identifier tied to the captured image of the imaging protocol information 307 is assigned to the imaging instruction, and the priority level of the instruction is set to high. After step S706 in FIG. 7, in step S801 in FIG. 8, an image targeted for re-imaging is then identified as the image captured on the imaging protocol information 307 from the image identifier incidental to the imaging instruction. In step S803, imaging protocol information with the same imaging region and position—"chest front—erect"—as those of the imaging protocol information on which the image targeted for re-imaging was captured is specified as for re-imaging. In step S804, the imaging success/failure status of the imaging protocol information 307 is changed to imaging failure. Next, after step S708, first in step S901, there is the imaging protocol information 311 in the imaging ready status. Execution then proceeds to step S902. In step S902, the priority level set in the imaging instruction is high. Execution then proceeds to step S904. In step S904, the imaging protocol information specified in step S803 is inserted after the imaging protocol information 311 in the imaging ready status. As a result of undergoing such a processing flow, what is displayed on the display unit 112 in step S709 is the imaging screen 301 illustrated in FIG. 10. The imaging protocol information 1002 is inserted in step S904. It can be seen that the imaging protocol information 1002 is inserted after the imaging protocol information 311 in the imaging ready status. It can be seen that due to the specification in step S803, the imaging region and position of the imaging protocol information 1002 are "chest front—erect" that are the same as those of the imaging protocol information 307 to which the image targeted for re-imaging is tied. The identifier 1003 indicating that the imaging protocol information 1002 has been added by the imaging instruction from the outside is displayed in the imaging protocol information 1002. On the other hand, in step S804, the imaging success/failure status of the captured image tied to the imaging protocol information 307 is changed to imaging failure. Accordingly, the identifier 1004 indicating imaging failure is displayed in the imaging protocol information 307. Even if the priority level is set to low in step S604, the display configuration is the same as that of FIG. 10. If the priority level is set to low, execution proceeds to step S905 in step S902. In step S905, the imaging region and position of the imaging protocol information 311 in the imaging ready status are "chest front—erect" that are the same as those of the imaging protocol information specified in step S803. Execution then proceeds to step S904. In step S904, the imaging protocol information specified in step S803 is added after the imaging protocol information 311 in the imaging ready status. Hence, the display is the same as that of FIG. 10.

Figure 11:
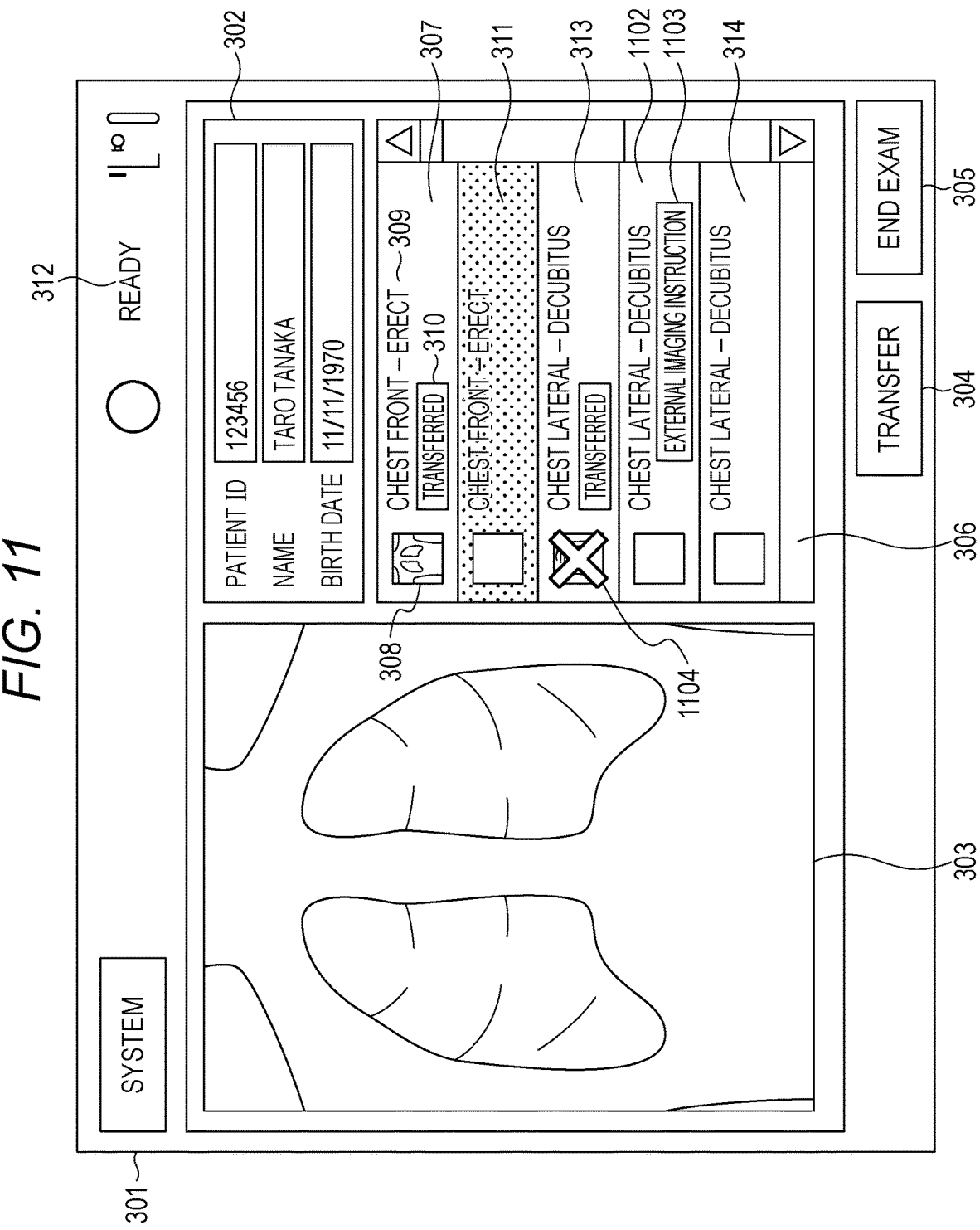
FIG. 11 is a diagram illustrating an example of the imaging screen after the addition of imaging protocol information according to the first to sixth embodiments.

FIG. 11 illustrates an example of the imaging screen after the addition of imaging protocol information by an external imaging instruction, the imaging screen being displayed on the display unit 112. The flow until the screen of FIG. 11 is displayed is specifically described. First, what is displayed on the display unit 112 is assumed to be the imaging screen 301 of FIG. 3. In step S505 in FIG. 5, the image captured on the imaging protocol information 313 of FIG. 3 is assumed to be transferred to the image quality assurance terminal 103 at the press of the transfer button 304 via the operation of the operating unit 113. It is assumed that the image displayed on the image quality assurance terminal 103 is then determined not to be of quality suitable for diagnosis in step S603 in FIG. 6, and an imaging instruction is transmitted in step S604. At this point in time, it is assumed that an image identifier tied to the captured image of the imaging protocol information 313 is assigned to the imaging instruction, and the priority level of the instruction is set to low. After step S706 in FIG. 7, in step S801 in FIG. 8, an image targeted for re-imaging is then identified as the image captured on the imaging protocol information 313 from the image identifier incidental to the imaging instruction. In step S803, imaging protocol information with the same imaging region and position—"chest lateral—decubitus"—as those of the imaging protocol information on which the image targeted for re-imaging was captured is specified as for re-imaging. In step S804, the imaging success/failure status of the imaging protocol information 313 is changed to imaging failure. Next, after step S708, first in step S901, there is the imaging protocol information 311 in the imaging ready status. Execution then proceeds to step S902. In step S902, the priority level set in the imaging instruction is low. Execution then proceeds to step S905. In step S905, the imaging region and position of the imaging protocol information 311 in the imaging ready status are "chest front—erect," and the imaging region and position of the imaging protocol information specified in step S803 are "chest lateral—decubitus." The imaging regions and positions are different. Execution then proceeds to step S907. In step S907, there is the unimaged imaging protocol information 314 with the same imaging region and position as those of the imaging protocol information specified in step S803. Execution then proceeds to step S911. In step S911, the imaging protocol information specified in step S803 is inserted immediately before the unimaged imaging protocol information 314. As a result of undergoing such a processing flow, what is displayed on the display unit 112 in step S709 is the imaging screen 301 illustrated in FIG. 11. Imaging protocol information 1102 is inserted in step S911. It can be seen that due to the specification in step S803, the imaging region and position of the imaging protocol information 1102 are "chest lateral—decubitus" that are the same as those of the imaging protocol information 313 to which the image targeted for re-imaging is tied. Moreover, it can be seen that due to the processing of step S911, the imaging protocol information 1102 is inserted immediately before the unimaged imaging protocol information 314 with the same imaging region and position. Moreover, a similar identifier 1103 to the identifier 1003 of FIG. 10 is displayed in the imaging protocol information 1102. On the other hand, in step S804, the imaging success/failure status of the captured image tied to the imaging protocol information 313 is changed to imaging failure. Accordingly, an identifier 1104 indicating imaging failure is displayed in the imaging protocol information 313.

Figure 12:
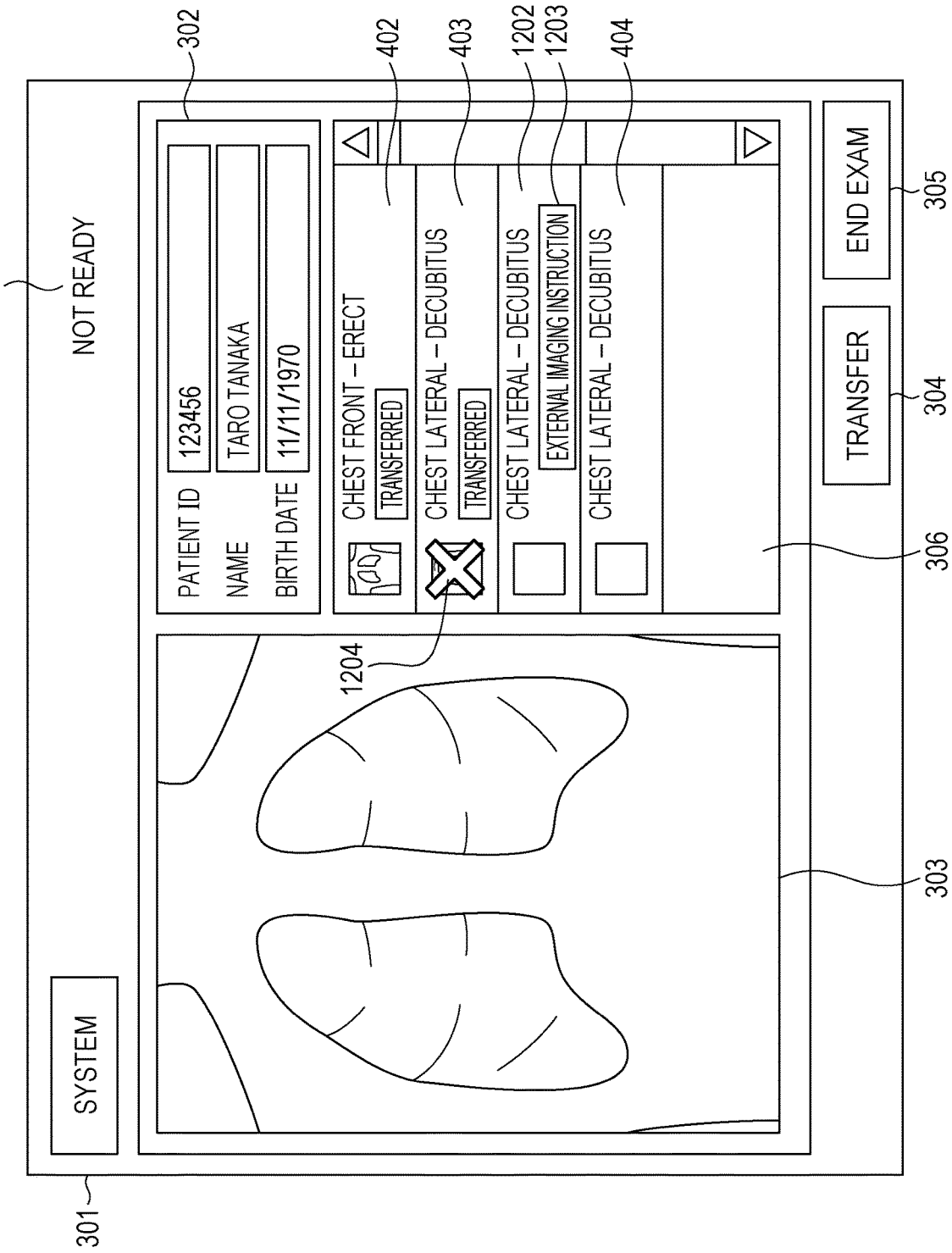
FIG. 12 is a diagram illustrating an example of the imaging screen after the addition of imaging protocol information according to the first to sixth embodiments.

FIG. 12 illustrates an example of the imaging screen after the addition of imaging protocol information by an external imaging instruction, the imaging screen being displayed on the display unit 112. The flow until the screen of FIG. 12 is displayed is specifically described. First, what is displayed on the display unit 112 is assumed to be the imaging screen 301 of FIG. 4. In step S505 in FIG. 5, the image captured on imaging protocol information 403 of FIG. 4 is assumed to be transferred to the image quality assurance terminal 103 at the press of the transfer button 304 via the operation of the operating unit 113. It is assumed that the image displayed on the image quality assurance terminal 103 is then determined not to be of quality suitable for diagnosis in step S603 in FIG. 6, and an imaging instruction is transmitted in step S604. At this point in time, it is assumed that an image identifier tied to the captured image of the imaging protocol information 403 is assigned to the imaging instruction, and the priority level of the instruction is set to low. After step S706 in FIG. 7, in step S801 in FIG. 8, an image targeted for re-imaging is then identified as the image captured on the imaging protocol information 403 from the image identifier incidental to the imaging instruction. In step S803, imaging protocol information with the same imaging region and position—"chest lateral—decubitus"—as those of the imaging protocol information on which the image targeted for re-imaging was captured is specified as for re-imaging. In step S804, the imaging success/failure status of the imaging protocol information 403 is changed to imaging failure. Next, after step S708, first in step S901, the examination order information on the imaging screen 301 includes no imaging protocol information in the imaging ready status. Execution then proceeds to step S903. In step S903, the priority level set in the imaging instruction is low. Execution then proceeds to step S907. In step S907, there is unimaged imaging protocol information 404 with the same imaging region and position as those of the imaging protocol information specified in step S803. Execution then proceeds to step S911. In step S911, the imaging protocol information specified in step S803 is inserted immediately before the unimaged imaging protocol information 404. As a result of undergoing such a processing flow, what is displayed on the display unit 112 in step S709 is the imaging screen 301 illustrated in FIG. 12. Imaging protocol information 1202 is inserted in step S911. It can be seen that due to the specification in step S803, the imaging region and position of the imaging protocol information 1202 are "chest lateral—decubitus" that are the same as those of the imaging protocol information 403 to which the image targeted for re-imaging is tied. Moreover, it can be seen that due to the processing of step S911, the imaging protocol information 1202 is inserted immediately before the imaging protocol information 404 to which the image targeted for re-imaging is tied. Moreover, a similar identifier 1203 to the identifier 1003 of FIG. 10 is displayed in the imaging protocol information 1202. On the other hand, in step S804, the imaging success/failure status of the captured image tied to the imaging protocol information 403 is changed to imaging failure. Accordingly, an identifier 1204 indicating imaging failure is displayed in the imaging protocol information 403. Even if the priority level is set to high in step S604, the display configuration is the same as that of FIG. 12. If the priority level is set to high, execution proceeds to step S906 in step S903. In step S906, a similar determination to that of step S907 is made. Execution then proceeds to step S908. In step S908, similar processing to that of step S911 is performed, as such, the display is the same as that of FIG. 12.

Figure 13:
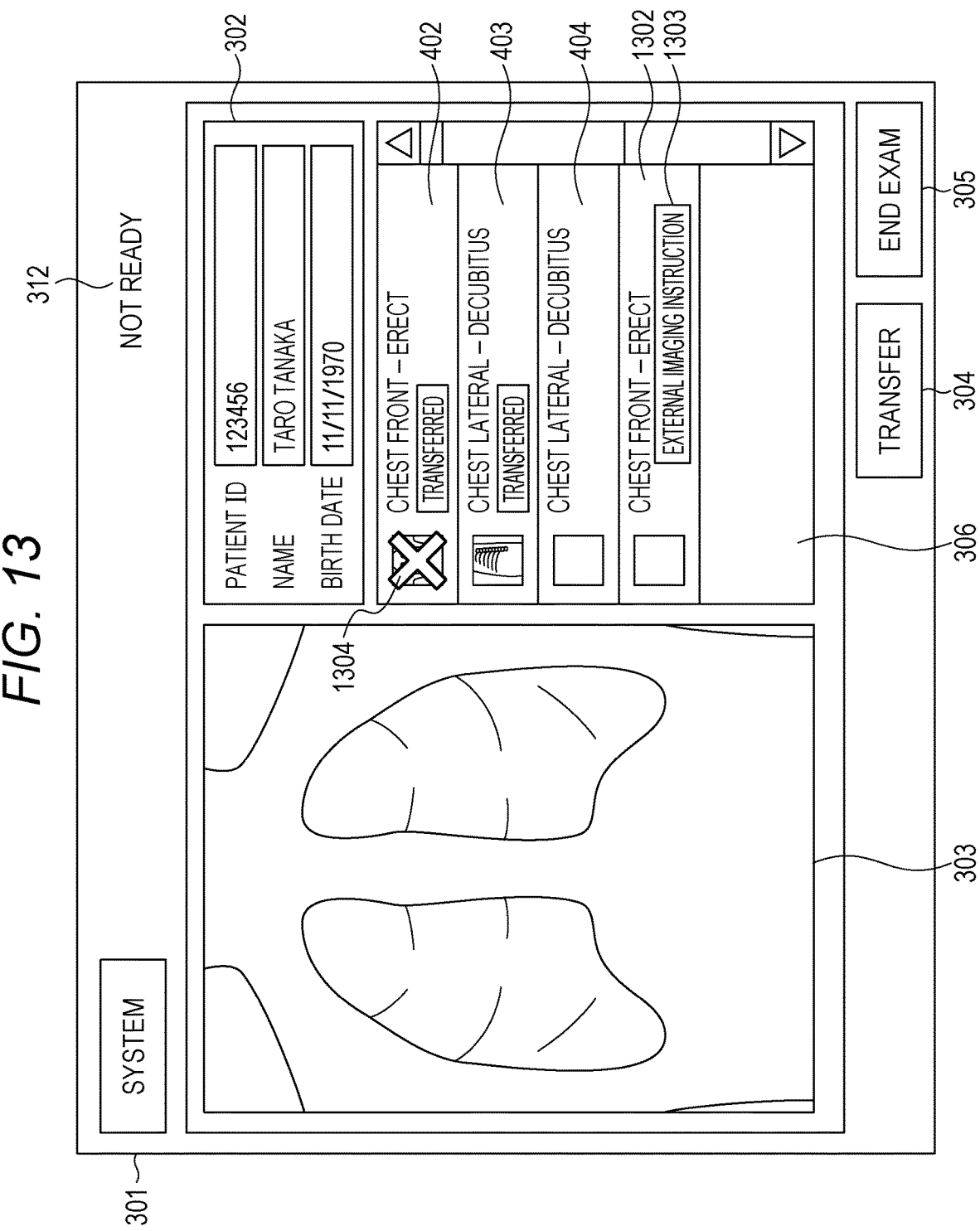
FIG. 13 is a diagram illustrating an example of the imaging screen after the addition of imaging protocol information according to the first to sixth embodiments.

FIG. 13 illustrates an example of the imaging screen after the addition of imaging protocol information by an external imaging instruction, the imaging screen being displayed on the display unit 112. The flow until the screen of FIG. 13 is displayed is specifically described. First, what is displayed on the display unit 112 is assumed to be the imaging screen 301 of FIG. 4. In step S505 in FIG. 5, the image captured on imaging protocol information 402 of FIG. 4 is assumed to be transferred to the image quality assurance terminal 103 at the press of the transfer button 304 via the operation of the operating unit 113. It is assumed that the image displayed on the image quality assurance terminal 103 is then determined not to be of quality suitable for diagnosis in step S603 in FIG. 6, and an imaging instruction is transmitted in step S604. At this point in time, it is assumed that an image identifier tied to the captured image of the imaging protocol information 402 is assigned to the imaging instruction, and the priority level of the instruction is set to low. After step S706 in FIG. 7, in step S801 in FIG. 8, an image targeted for re-imaging is then identified as the image captured on the imaging protocol information 402 from the image identifier incidental to the imaging instruction. In step S803, imaging protocol information with the same imaging region and position—"chest front—erect"—as those of the imaging protocol information on which the image targeted for re-imaging was captured is specified as for re-imaging. In step S804, the imaging success/failure status of the imaging protocol information 402 is changed to imaging failure. Next, after step S708, first in step S901, the examination order information on the imaging screen 301 includes no imaging protocol information in the imaging ready status. Execution then proceeds to step S903. In step S903, the priority level set in the imaging instruction is low. Execution then proceeds to step S907. In step S907, there is no unimaged imaging protocol information with the same imaging region and position—"chest front—erect"—as those of the imaging protocol information specified in step S803. Execution then proceeds to step S912. In step S912, the imaging protocol information specified in step S803 is inserted at the bottom of the list of the imaging protocol information. As a result of undergoing such a processing flow, what is displayed on the display unit 112 in step S709 is the imaging screen 301 illustrated in FIG. 13. Imaging protocol information 1302 is inserted in step S912. It can be seen that due to the specification in step S803, the imaging region and position of the imaging protocol information 1302 are "chest front—erect" that are the same as those of the imaging protocol information 402 to which the image targeted for re-imaging is tied. Moreover, it can be seen that due to the processing of step S912, the imaging protocol information 1302 is inserted at the bottom of the list. Moreover, a similar identifier 1303 to the identifier 1003 of FIG. 10 is displayed in the imaging protocol information 1302. On the other hand, in step S804, the imaging success/failure status of the captured image tied to the imaging protocol information 402 is changed to imaging failure. Accordingly, an identifier 1304 indicating imaging failure is displayed in the imaging protocol information 402.

FIG. 14 illustrates an example of the imaging screen after the addition of imaging protocol information by an external imaging instruction, the imaging screen being displayed on the display unit 112. The flow until the screen of FIG. 14 is displayed is specifically described. First, what is displayed on the display unit 112 is assumed to be the imaging screen 301 of FIG. 4. In step S505 in FIG. 5, the image captured on the imaging protocol information 402 of FIG. 4 is assumed to be transferred to the image quality assurance terminal 103 at the press of the transfer button 304 via the operation of the operating unit 113. It is assumed that the image displayed on the image quality assurance terminal 103 is then determined not to be of quality suitable for diagnosis in step S603 in FIG. 6, and an imaging instruction is transmitted in step S604. At this point in time, it is assumed that an image identifier tied to the captured image of the imaging protocol information 402 is assigned to the imaging instruction, and the priority level of the instruction is set to high. After step S706 in FIG. 7, in step S801 in FIG. 8, an image targeted for re-imaging is then identified as the image captured on the imaging protocol information 402 from the image identifier incidental to the imaging instruction. In step S803, imaging protocol information with the same imaging region and position—"chest front—erect"—as those of the imaging protocol information on which the image targeted for re-imaging was captured is specified as for re-imaging. In step S804, the imaging success/failure status of the imaging protocol information 402 is changed to imaging failure. Next, after step S708, first in step S901, the examination order information on the imaging screen 301 includes no imaging protocol information in the imaging ready status. Accordingly, execution proceeds to step S903. In step S903, the priority level set in the imaging instruction is high, and execution proceeds to step S906. In step S906, there is no unimaged imaging protocol information with the same imaging region and position—"chest front—erect"—as those of the imaging protocol information specified in step S803, and execution proceeds to step S909. In step S909, the imaging protocol information specified in step S803 is inserted at the top of the list of the imaging protocol information. As a result of undergoing such a processing flow, what is displayed on the display unit 112 in step S709 is the imaging screen 301 illustrated in FIG. 14. Imaging protocol information 1402 is inserted in step S909. It can be seen that due to the specification in step S803, the imaging region and position of the imaging protocol information 1402 are "chest front—erect" that are the same as those of the imaging protocol information 402 to which the image targeted for re-imaging is tied. Moreover, it can be seen that due to the processing of step S909, the imaging protocol information 1402 is inserted at the top of the list. Moreover, a similar identifier 1403 to the identifier 1003 of FIG. 10 is displayed in the imaging protocol information 1402. On the other hand, in step S804, the imaging success/failure status of the captured image tied to the imaging protocol information 402 is changed to imaging failure. Accordingly, an identifier 1404 indicating imaging failure is displayed in the imaging protocol information 402.

Figure 15:
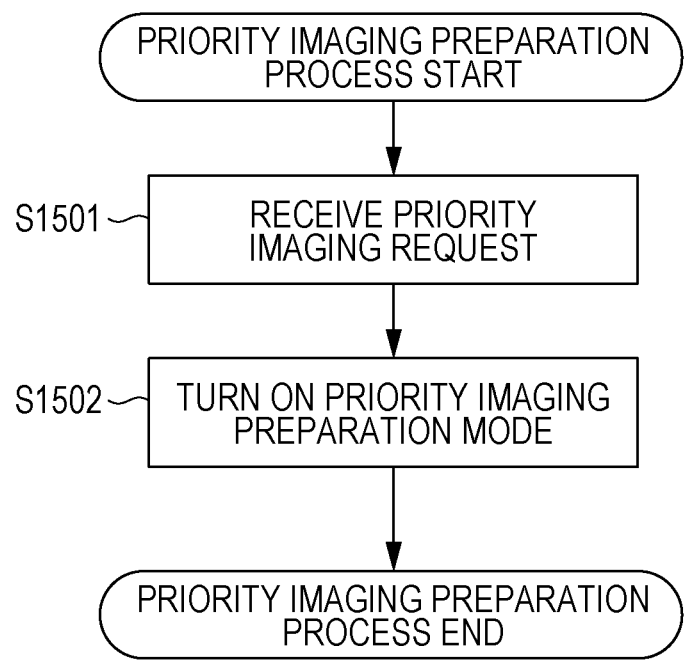
FIG. 15 is a flowchart illustrating an example of a priority imaging preparation process according to the first to sixth embodiments.

A description is given of the flow of a priority imaging preparation process of when the imaging preparation control unit 216 receives the priority imaging preparation request during examination in step S910, with reference to FIG. 15. In the following description, "during examination" indicates a situation from the start to the end of the examination in FIG. 5, that is, from steps S502 to S507. Such a process is executed mainly by the imaging control device 111.

First in step S1501, the imaging preparation control unit 216 receives the priority imaging preparation request requested in step S910. The priority imaging preparation request includes an identifier that uniquely identifies the imaging protocol information inserted in step S908 or S909. Next, execution proceeds to step S1502.

In step S1502, the identifier of the imaging protocol information included in the priority imaging preparation request received in step S1501 is stored in the imaging preparation control unit 216. Next, execution proceeds to step S1503.

In step S1503, the imaging preparation control unit 216 makes a transition to priority imaging preparation mode to end the priority imaging preparation process.

Figure 16:
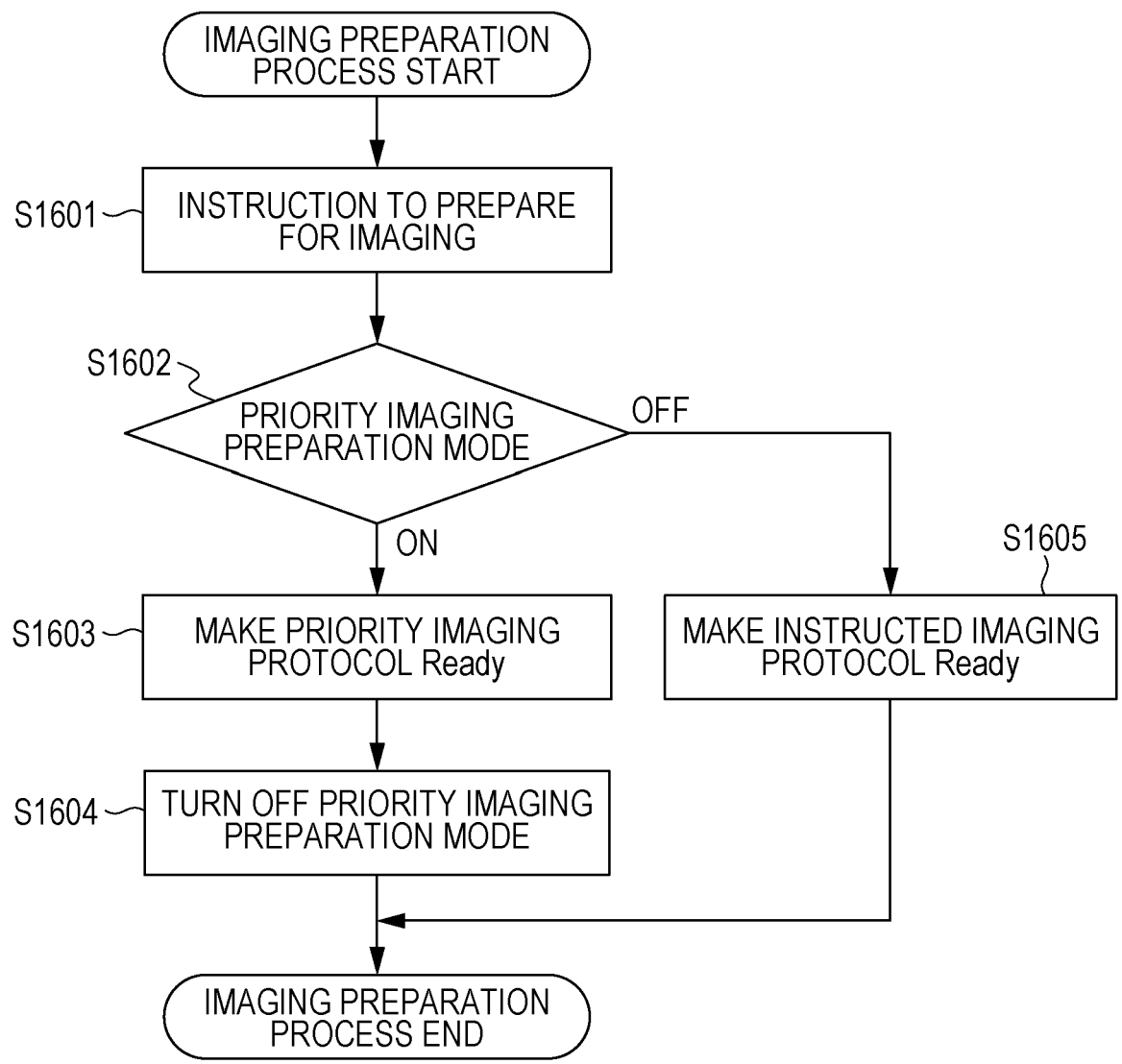
FIG. 16 is a flowchart illustrating an example of an imaging preparation process according to the first to sixth embodiments.

A description is given of the flow of an imaging preparation process where the imaging preparation control unit 216 changes imaging protocol information to the imaging ready status during examination, with reference to FIG. 16. It is specific processing of step S503 in FIG. 5. Such a process is executed mainly by the imaging control device 111.

First in step S1601, an imaging preparation is instructed in response to an operation by the operator or by the imaging preparation control unit 216 itself. Next, execution proceeds to step S1602.

In step S1602, the imaging preparation control unit 216 determines whether to be in priority imaging preparation mode. If in priority imaging preparation mode, execution proceeds to step S1603. If not, execution proceeds to step S1605.

In step S1603, the imaging preparation control unit 216 changes the imaging protocol information tied to the identifier stored in step S1502 in FIG. 15 to the imaging ready status. Next, execution makes a transition to step S1604.

In step S1604, the imaging preparation control unit 216 cancels the priority imaging preparation mode to end the imaging preparation process.

In step S1605, imaging protocol information as instructed on imaging preparation in step S1601 is changed to the imaging ready status to end the imaging preparation process.

Figure 17:
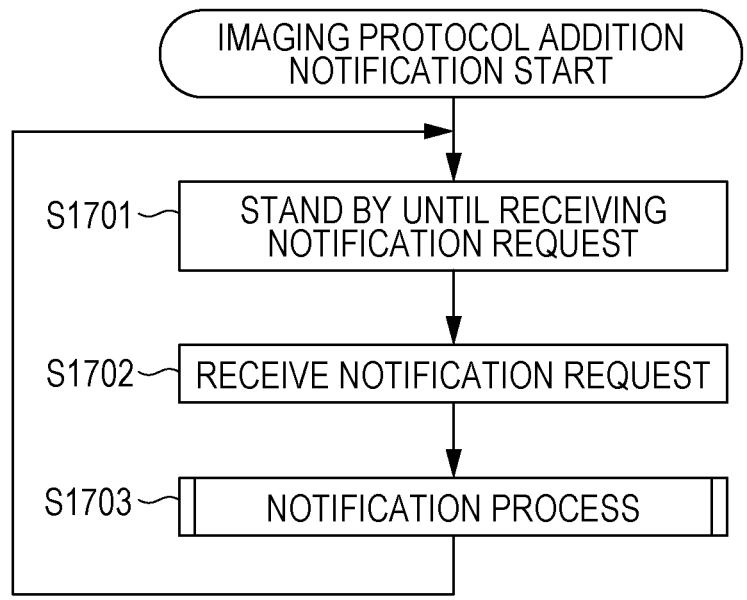
FIG. 17 is a flowchart illustrating an example of an imaging protocol information addition notification process according to the first embodiment.

A description is given of the flow of an imaging protocol information addition notification process of when the notification unit 214 receives a notification request during examination, with reference to FIG. 17. Such a process is executed mainly by the imaging control device 111.

First in step S1701, the notification unit 214 stands by until the notification request of step S806 in FIG. 8 is transmitted. When a notification request has been transmitted, execution proceeds to step S1702.

In step S1702, the notification unit 214 receives the notification request of step S806 in FIG. 8. Next, execution proceeds to step S1703.

Figure 18:
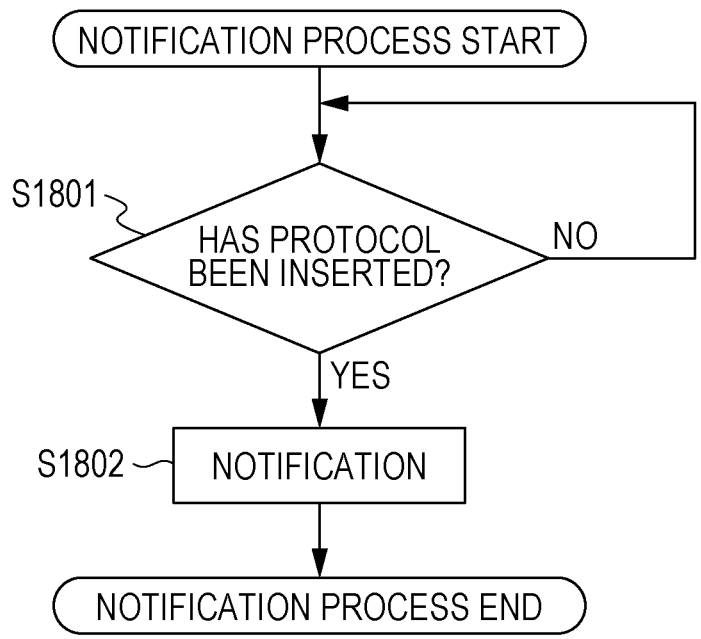
FIG. 18 is a flowchart illustrating a specific example of the imaging protocol information addition notification process according to the first embodiment.

Specific processing of step S1703 is described in FIG. 18. After the processing of step S1703, execution returns to step S1701.

A description is given of a specific processing flow of the notification process by then notification unit 214, with reference to FIG. 18. Such a process is executed mainly by the imaging control device 111.

First in step S1801, it is determined whether the position specification unit 215 has inserted imaging protocol information into examination order information. If inserted, execution proceeds to step S1802. If not, execution returns to step S1801.

In step S1802, a notification screen 1901 illustrated in FIG. 19 is displayed on the display unit 112. As indicated by a reference numeral 1902, the priority level and reason of an imaging instruction stored in the imaging instruction storage unit 206 can be displayed. The notification process ends after the display.

Figure 20:
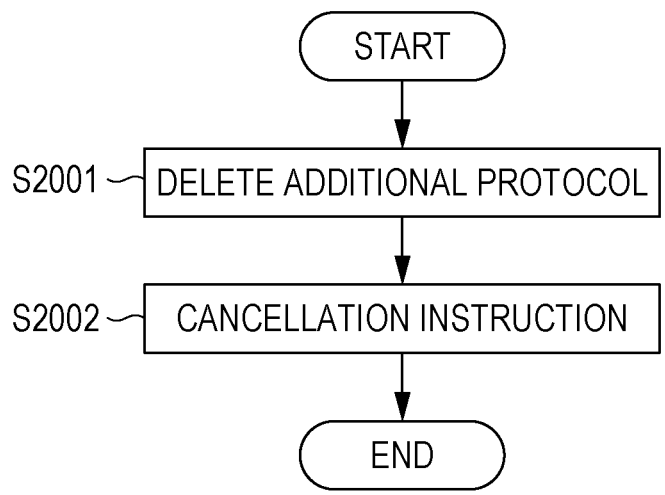
FIG. 20 is a flowchart illustrating an example of a cancellation instruction process according to the first to sixth embodiments.
Figure 21:
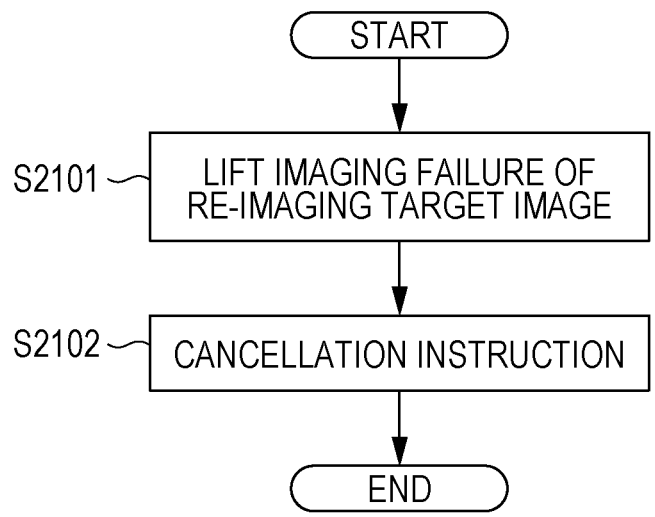
FIG. 21 is a flowchart illustrating an example of a cancellation instruction process according to the first to fourth embodiments.
Figure 22:
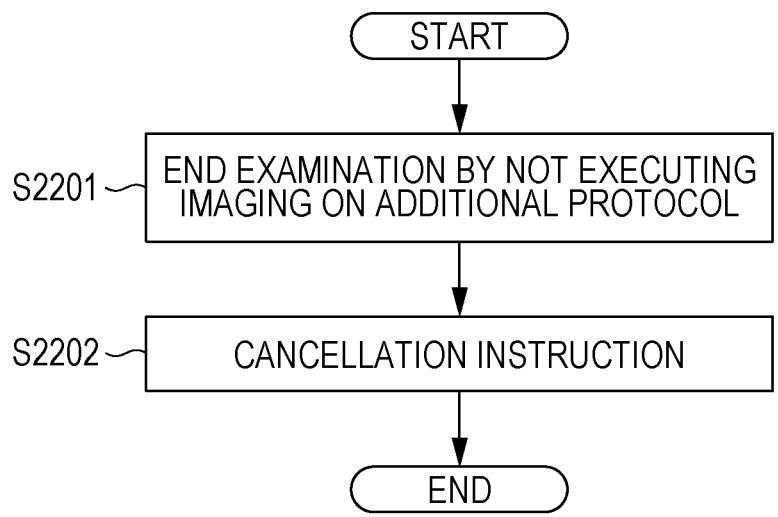
FIG. 22 is a flowchart illustrating an example of a cancellation instruction process according to the first to sixth embodiments.

What is described next in FIGS. 20, 21, and 22 is the contents of a process where if imaging is not performed with imaging protocol information added by an imaging instruction from the outside, a cancellation instruction is notified to an imaging instruction giving side.

A description is given of the flow of a process of when the imaging protocol information inserted by the position specification unit 215 is deleted, with reference to FIG. 20. Such a process is executed mainly by the imaging control device 111.

First in step S2001, the imaging protocol information inserted by the position specification unit 215 is deleted in response to the operation of the operating unit 113 before the end of the examination for reasons such as that imaging on the inserted imaging protocol information is not required. Next, execution proceeds to step S2002.

In step S2002, in response to the deletion of the imaging protocol information in step S2001, the cancellation instruction unit 208 transmits a cancellation instruction to an imaging instruction input side via the imaging instruction receiving unit 205.

A description is given of a process of when imaging failure of an image targeted for re-imaging is lifted, with reference to FIG. 21. Such a process is executed mainly by the imaging control device 111.

First in step S2101, the captured image whose imaging success/failure status was changed to imaging failure in step S804 in FIG. 8 is determined not to be an imaging failure in accordance with the input of an operation by the operator. Imaging failure is lifted via the operation of the operating unit 113 in response to the input of an operation by the operator. Next, execution proceeds to step S2102.

In step S2102, in response to the lifting of imaging failure in step S2101, the cancellation instruction unit 208 transmits a cancellation instruction to an imaging instruction input side via an external imaging instruction input unit.

A description is given of the flow of a process of when the examination ends while imaging on the imaging protocol information inserted by the position specification unit 215 is left unperformed, with reference to FIG. 22. Such a process is executed mainly by the imaging control device 111.

First in step S2201, the examination ends at the press of the end exam button 305 via the operation of the operating unit 113 while imaging on the inserted imaging protocol information is left unperformed. Such a process is performed for reasons such as that imaging on the imaging protocol information inserted by the position specification unit 215 is not required. Next, execution proceeds to step S2202.

In step S2202, in response to the end of the examination in step S2201, the cancellation instruction unit 208 transmits a cancellation instruction to an imaging instruction input side via the external imaging instruction input unit.

As described above, according to the first embodiment, when an imaging instruction has been received from the outside during examination, the instructed imaging protocol information can be automatically added to examination order information. Consequently, it is possible to prevent a mistake in selecting additional imaging protocol information and forgetting to add imaging protocol information due to the carelessness of the operator. At this point in time, the addition is notified to the operator immediately after the addition. Accordingly, the operator can recognize that the imaging protocol information has been added. Furthermore, in synchronization with the notification, the priority level and reason of the imaging instruction can be discovered. Furthermore, the identifier that indicates the addition is displayed in imaging protocol information. As such, the operator can distinguish between the imaging protocol information added by the imaging instruction from the outside and imaging protocol information that is not added by an imaging instruction from the outside.

Moreover, the status of a captured image targeted for re-imaging is automatically changed to imaging failure. Accordingly, it is possible to prevent forgetting to change the imaging success/failure status due to the carelessness of the operator. Furthermore, an imaging instruction reason is added to an imaging failure reason for the captured image that has turned to be an imaging failure. Accordingly, it is possible to later discover why the captured image has turned to be an imaging failure. Furthermore, the operator can identify the captured image that has turned to be an imaging failure as transferred and imaging failure based on the display of the identifiers.

Moreover, if imaging protocol information cannot be added since the number of pieces of imaging protocol information and the number of radiation doses in examination order information have reached their upper limits, or if imaging on additional imaging protocol information is not performed based on a determination by the operator, a cancellation instruction is automatically transmitted to an imaging instruction transmission side. Consequently, it is possible to convey information to the effect that the imaging protocol information could not be added without forgetting it.

Moreover, it becomes possible to insert additional imaging protocol information at an appropriate position and take an X-ray preferentially if a high-priority imaging instruction has been received. Furthermore, if the priority level is not high, the additional imaging protocol is inserted immediately before imaging protocol information with the same imaging region and position. Accordingly, the burden of a change in position on a patient caused by re-imaging can be reduced.

On the whole, inconvenience that can occur when an imaging instruction is received from the outside is eliminated to improve the correctness of an imaging operation.

Second Embodiment

Next, a second embodiment is described.

The second embodiment is similar to the first embodiment, and as such, only the differences in the second embodiment will be discussed below.

Figure 23:
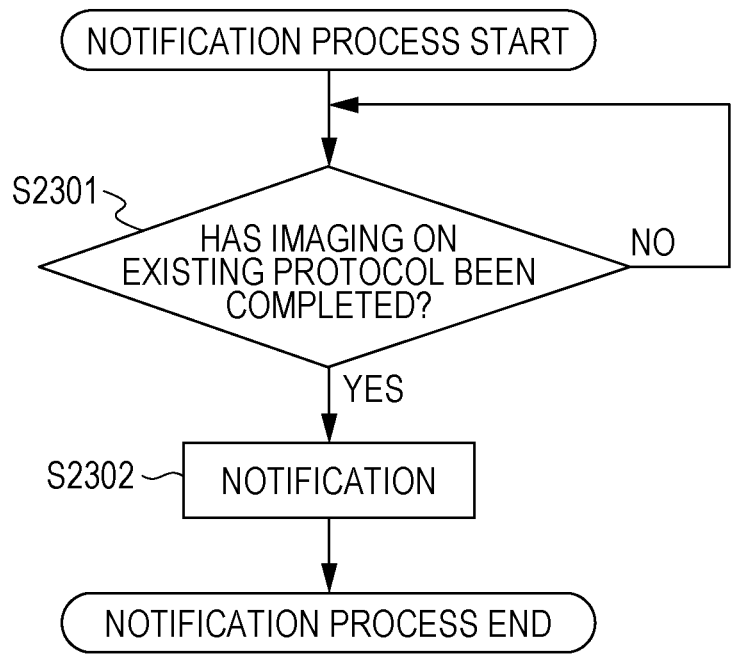
FIG. 23 is a flowchart illustrating a specific example of an imaging protocol information addition notification process according to the second embodiment.

Specific processing of step S1702 in FIG. 17 is described in FIG. 23.

A description is given of a specific processing flow of the notification process by the notification unit 214, with reference to FIG. 23. Such a process is executed mainly by the imaging control device 111.

First in step S2301, it is determined whether imaging on existing imaging protocol information of examination order information other than the imaging protocol information inserted by the position specification unit 215 has been completed. If completed, execution proceeds to step S2302. If not, execution returns to step S2301.

The processing of step S2302 is similar to that of step S1802 in FIG. 18 described in the first embodiment.

As described above, the effects of the second embodiment are similar to those of the first embodiment other than a difference. Only the difference is described. Information to the effect that the imaging protocol information has been added by an external imaging instruction is notified at the timing when imaging on the existing imaging protocol information is completed. Accordingly, it is possible to notify the addition to an operator without interfering with an imaging operation on the existing imaging protocol information and an image processing operation by the operator. On the whole, inconvenience that can occur when an imaging instruction is received from the outside is eliminated to improve the correctness of the imaging operation.

Third Embodiment

Next, a third embodiment is described.

The third embodiment is similar to the first embodiment, and as such, only differences in the third embodiment will be discussed below.

Figure 24:
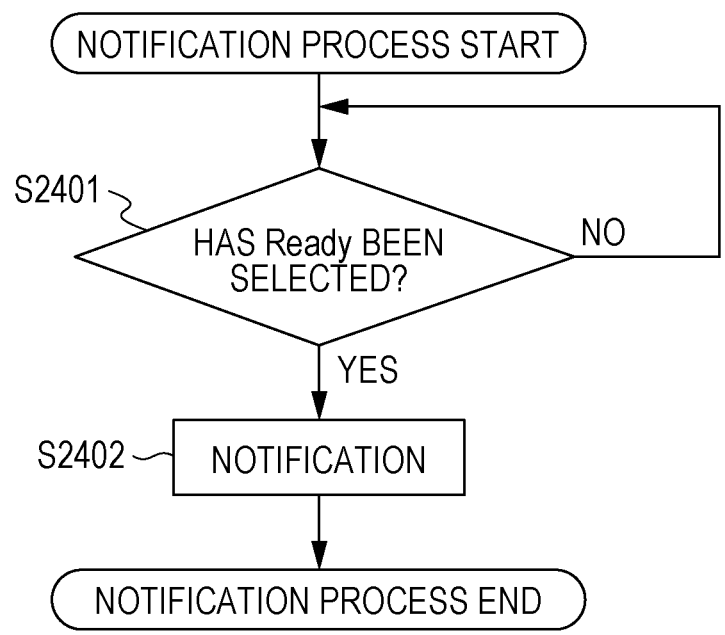
FIG. 24 is a flowchart illustrating a specific example of an imaging protocol information addition notification process according to the third embodiment.

Specific processing of step S1702 in FIG. 17 is described in FIG. 24.

A description is given of a specific processing flow of the notification process by the notification unit 214, with reference to FIG. 24. Such a process is executed mainly by the imaging control device 111.

First in step S2401, it is determined whether the imaging preparation control unit 216 has changed the imaging protocol information inserted by the position specification unit 215 to the imaging ready status. If the imaging protocol information inserted by the position specification unit 215 has been changed, execution proceeds to step S2402. If not, execution returns to step S2401.

The processing of step S2402 is similar to that of step S1802 in FIG. 18.

As described above, the effects of the third embodiment are similar to those of the first embodiment, as such, only the differences will be described. Information to the effect that imaging protocol information was added by an external imaging instruction is notified at a time when the added imaging protocol information was changed to the imaging ready status. Accordingly, it is possible to notify the addition to an operator without interfering with an imaging operation on existing imaging protocol information and an image processing operation by the operator. On the whole, inconvenience that can occur when an imaging instruction is received from the outside is eliminated to improve the correctness of the imaging operation.

Fourth Embodiment

Next, a fourth embodiment is described.

An X-ray imaging system to which a radiographic imaging system is applied according to the fourth embodiment is similar to that of the first embodiment as illustrated in FIG. 1.

Figure 2:
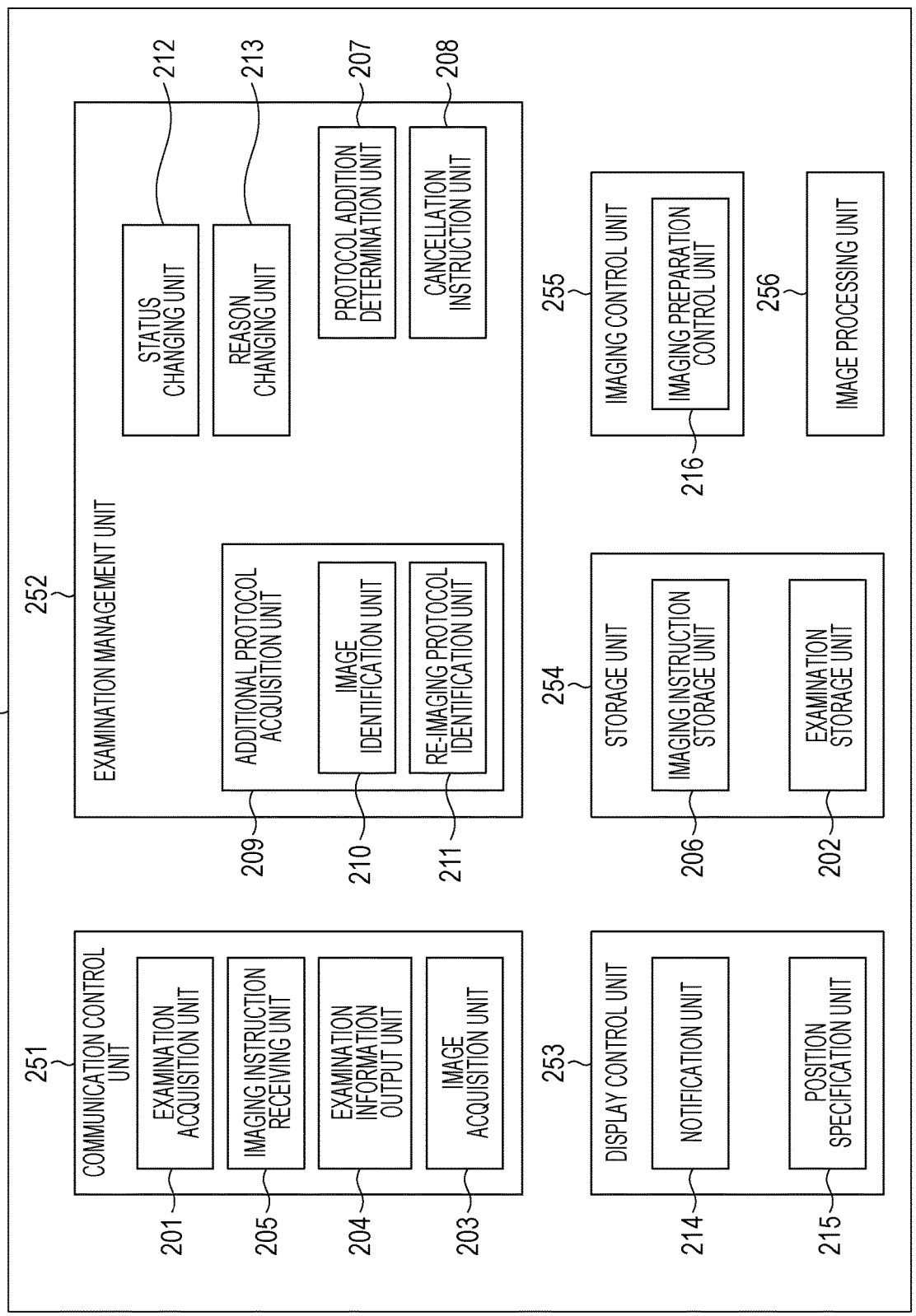
FIG. 2 is a diagram illustrating an example of a functional configuration of an imaging control device 111 according to the first embodiment.

Moreover, a functional configuration of the imaging control device 111 illustrated in FIG. 1, the functional configuration realizing the fourth embodiment, is similar to that of FIG. 2. Accordingly, its description is omitted.

Moreover, in terms of a description of the fourth embodiment, an example of a screen displayed on the display unit 112 is similar to that of FIG. 32 used to describe the first embodiment.

A specific example of a processing flow according to the fourth embodiment is cited.

Figure 5:
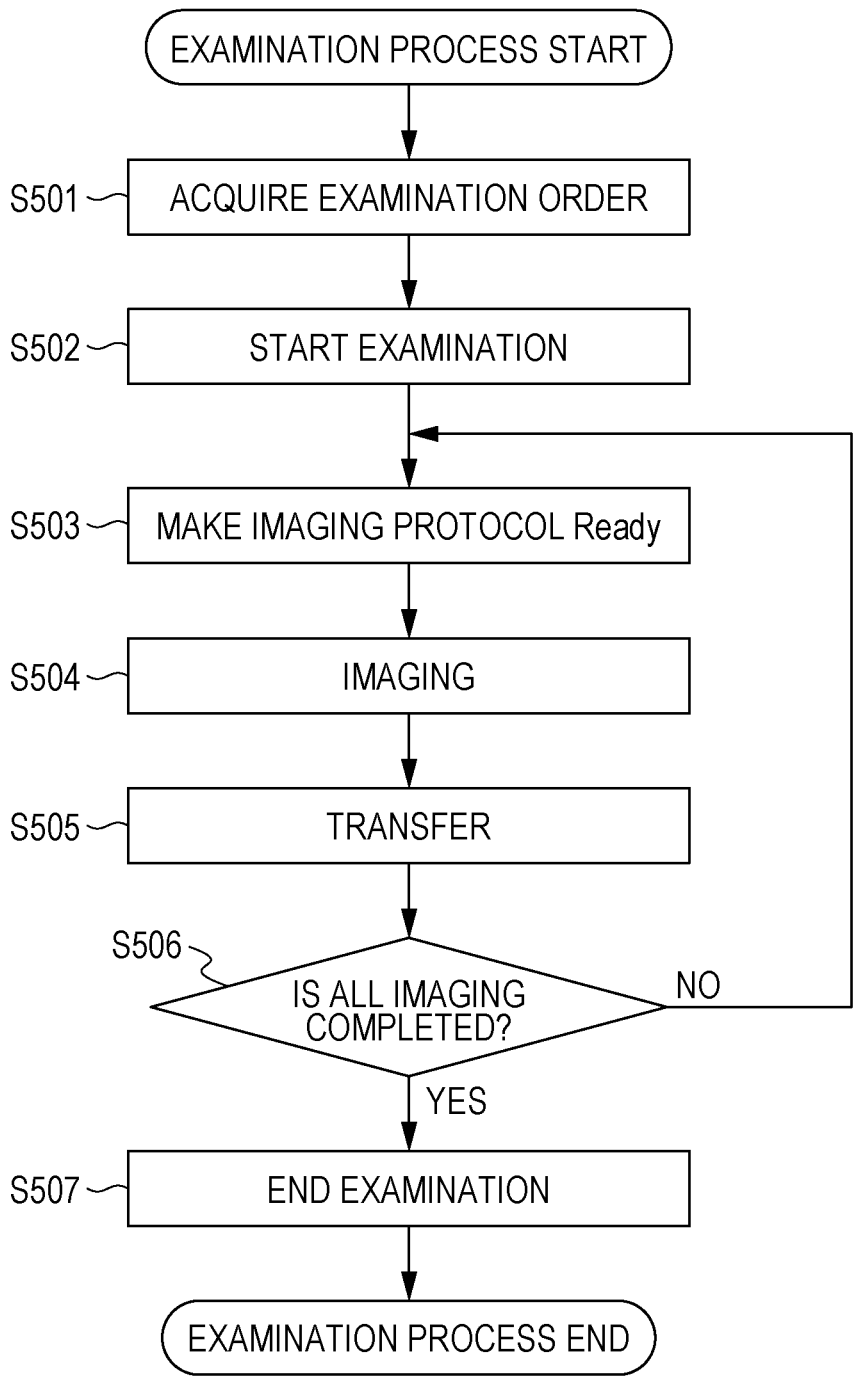
FIG. 5 is a flowchart illustrating an example showing the start to the end of an examination according to the first to sixth embodiments.

A series of procedures from the start of to the end of an examination is similar to procedures described in FIG. 5 of the first embodiment.

The flow of an image quality assurance process in the image quality assurance terminal 103 is similar to the flow described in FIG. 6 of the first embodiment.

The flow of a process of adding imaging protocol information based on an imaging instruction received by the imaging control device 111 during examination is similar to the one described in FIG. 7 of the first embodiment. However, only differences are described.

Figure 25:
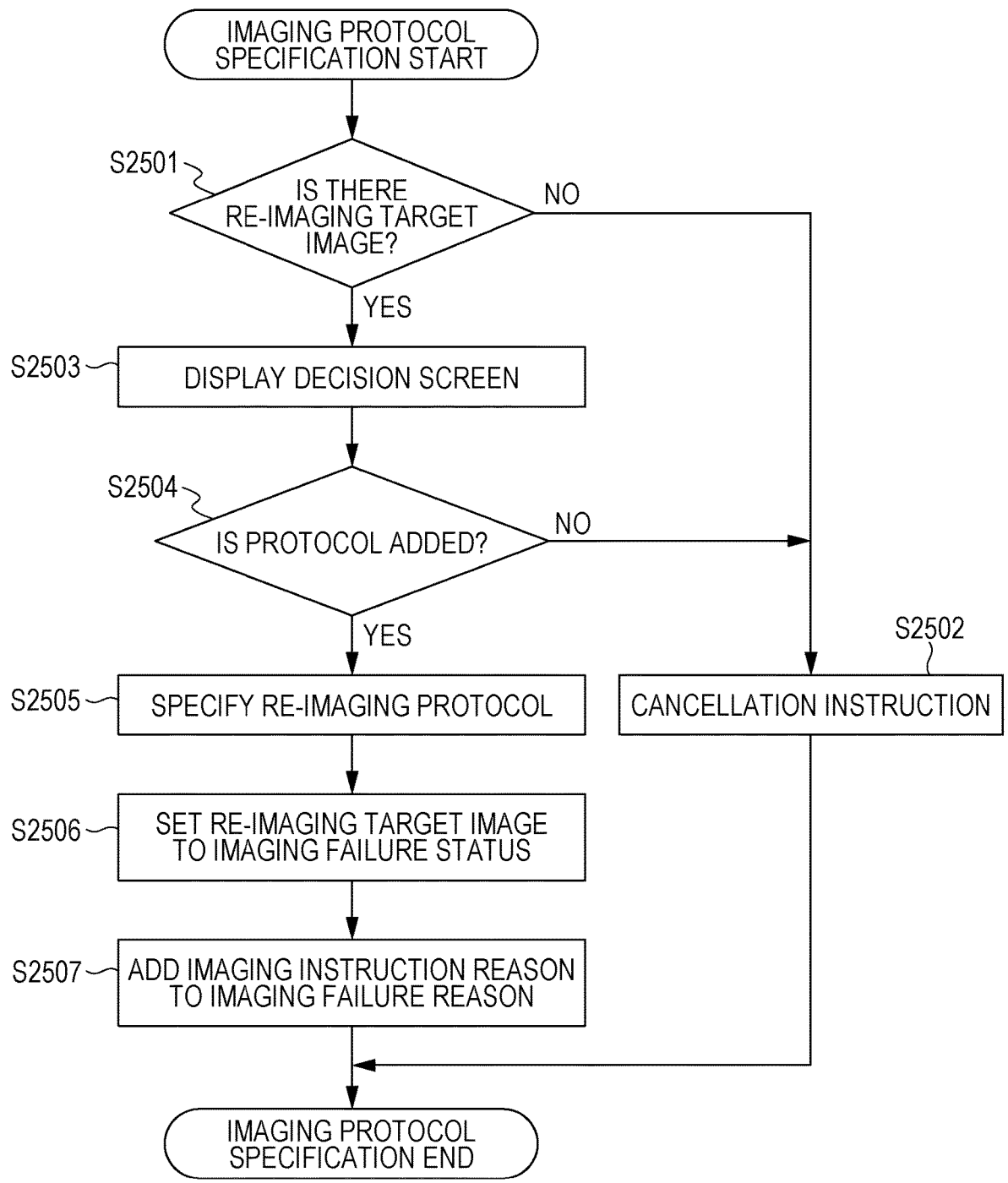
FIG. 25 is a flowchart illustrating an example of an imaging protocol information specification process according to the fourth embodiment.

A specific processing flow of step S706 is described in accordance with the flowchart of FIG. 25. Such processing is executed mainly by the imaging control device 111.

First, the processing of step S2501 is similar to that of step S801. If an applicable captured image cannot be found, execution proceeds to step S2502. If an applicable captured image can be found, the found captured image is identified as a re-imaging target, and execution proceeds to step S2503.

The processing of step S2502 is similar to that of step S704. Next, execution proceeds to step S707 of FIG. 7.

In step S2503, such a screen 2601 as illustrated in FIG. 26, the screen 2601 prompting an operator to determine whether to add imaging protocol information, is displayed on the display unit 112. As indicated by a reference numeral 2602, the priority level and reason of an imaging instruction stored in the imaging instruction storage unit 206 can be displayed. Next, execution proceeds to step S2504.

In step S2504, it is determined to add the imaging protocol information in response to the input of an operation of pressing a yes button 2603 by the operator who has viewed the contents of the reference numerals 2601 and 2602. Next, execution proceeds to step S2504. If there is the input of an operation of pressing the cancel button 2604 via the operating unit 113, it is determined not to add the imaging protocol information. Execution proceeds to step S2502.

The processing of step S2505 is similar to that of step S803. Next, execution proceeds to step S2506.

The processing of step S2506 is similar to that of step S804. Next, execution proceeds to step S2507.

The processing of step S2507 is similar to that of step S805. Next, execution proceeds to step S707 in FIG. 7.

Specific processing of step S708 in FIG. 7 is similar to the one described in FIG. 9 in the first embodiment.

Examples of the insertion position of the imaging protocol information on the imaging screen in step S709 in FIG. 7 are similar to those of FIGS. 10, 11, 12, 13, and 14 described in the first embodiment. However, when steps S801, S803, S804, and S805 are replaced with steps S2501, S2505, S2506, and S2507, respectively, in the descriptions using FIGS. 10, 11, 12, 13, and 14, respectively, in the first embodiment, the fourth embodiment can be described as similar processing to that of the first embodiment.

The flow of a priority imaging preparation process of when the imaging preparation control unit 216 receives a priority imaging preparation request in step S910 during examination is similar to the one described in FIG. 15 in the first embodiment.

The flow of an imaging preparation process where the imaging preparation control unit 216 changes imaging protocol information to the imaging ready status is similar to the one described in FIG. 16 in the first embodiment.

When imaging is not performed with imaging protocol information added by an imaging instruction from the outside, the content of a process of notifying a cancellation instruction to an imaging instruction giving side is similar to those described in FIGS. 20, 21, and 22 in the first embodiment.

As described above, according to the fourth embodiment, when an imaging instruction is received from the outside during examination, it is possible to check whether to add imaging protocol information. At this point in time, it is possible to discover the priority level and reason of the imaging instruction. When it has been determined that the operator adds the imaging protocol information, the instructed imaging protocol information becomes possible to be added to the examination order information. It is possible to prevent a mistake in selecting additional imaging protocol information and forgetting to add imaging protocol information due to the carelessness of the operator.

The status of a captured image targeted for re-imaging is automatically changed to imaging failure. Accordingly, it is possible to prevent forgetting to change the imaging success/failure status due to the carelessness of the operator. Furthermore, an imaging instruction reason is added to an imaging failure reason for the captured image that has turned to be an imaging failure. Thus, it is possible to later discover why the captured image turned to be an imaging failure. Furthermore, the operator can identify the captured image turned to be an imaging failure as transferred and imaging failure based on the display of the identifiers.

Moreover, if imaging protocol information cannot be added since the number of pieces of imaging protocol information and the number of radiation doses in examination order information have reached their upper limits, of if imaging on additional imaging protocol information is not performed based on the operator's determination, a cancellation instruction is automatically transmitted to an imaging instruction transmission side. Consequently, it is possible to convey information to the effect that the imaging protocol information could not be added without forgetting it.

Moreover, when a high-priority imaging instruction is received, it becomes possible to insert the additional imaging protocol information at an appropriate position and take an X-ray preferentially. Furthermore, if the priority level is not high, the additional imaging protocol information is inserted immediately before imaging protocol information with the same imaging region and position. Accordingly, it is possible to reduce the burden of a change in position on a patient caused by re-imaging.

On the whole, inconvenience that can occur when an imaging instruction is received from the outside is eliminated to improve the correctness of an imaging operation.

Fifth Embodiment

Next, a fifth embodiment is described.

An X-ray imaging system to which a radiographic imaging system is applied according to the fifth embodiment is similar to that of the first embodiment illustrated in FIG. 1.

Moreover, a functional configuration of the imaging control device 111 illustrated in FIG. 1, the functional configuration realizing the fifth embodiment, is similar to that of FIG. 2. An imaging protocol information candidate extraction unit 2801 extracts candidates for imaging protocol information to be added to examination order information based on an imaging instruction. The additional protocol acquisition unit 209 includes the imaging protocol information candidate extraction unit 2801.

Moreover, in terms of a description of the fifth embodiment, an example of a screen displayed on the display unit 112 is similar to that of FIG. 32 used to describe the first embodiment.

A specific example of a processing flow according to the fifth embodiment is cited.

A series of procedures from the start of to the end of an examination is similar to the procedures described in FIG. 5 of the first embodiment.

Figure 27:
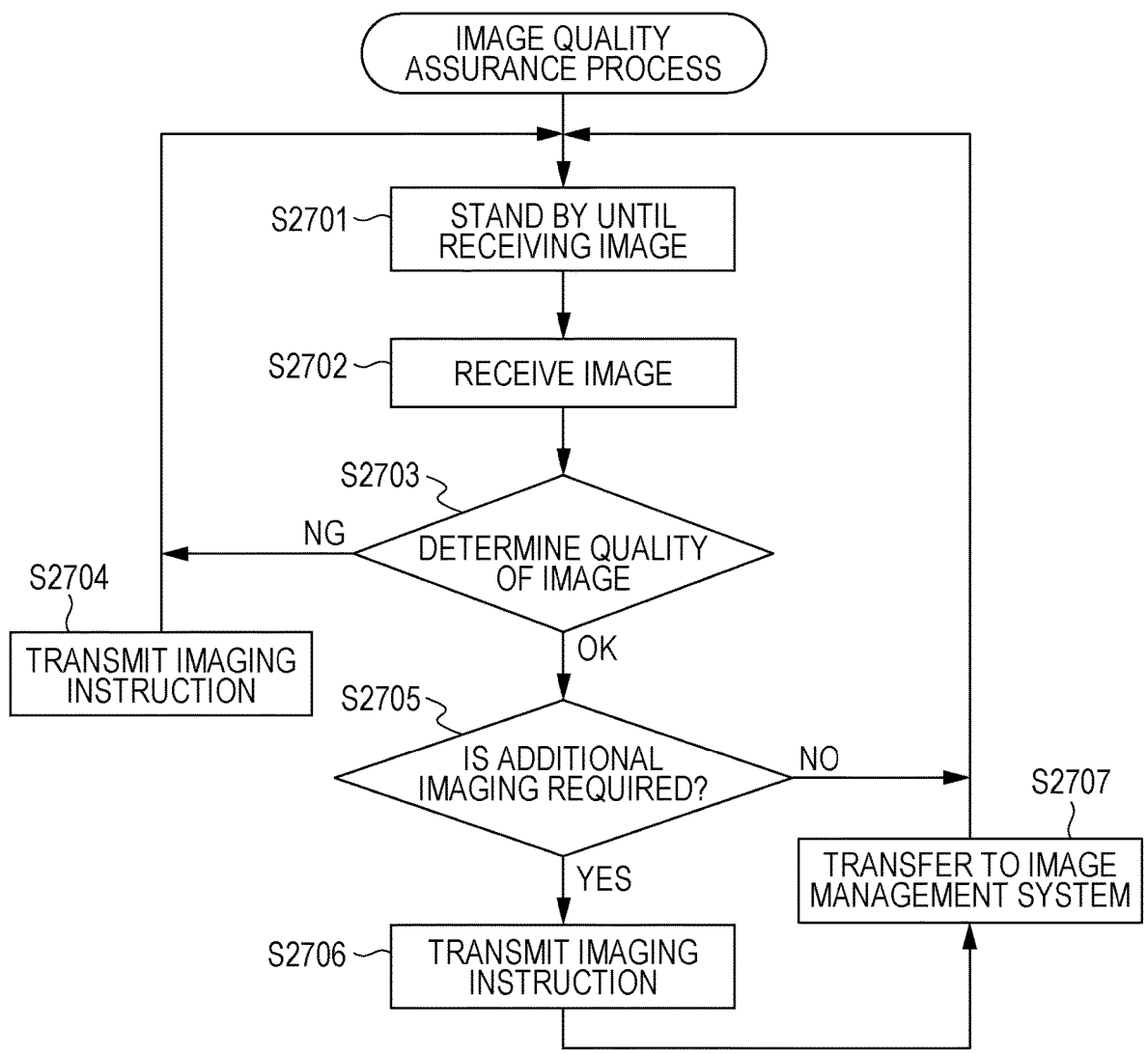
FIG. 27 is a flowchart illustrating an example of an image quality assurance process according to the fifth and sixth embodiments.

The flow of an image quality assurance process of the image quality assurance terminal 103 is described with reference to FIG. 27. Such a process is executed mainly by the image quality assurance terminal 103.

First, the processing of step S2701 is similar to that of step S601 in the first embodiment. Next, execution proceeds to step S2702.

The processing of step S2702 is similar to that of step S602 in the first embodiment. Next, execution proceeds to step S2703.

In step S2703, the captured image displayed on the image quality assurance terminal 103 is determined whether to be of quality suitable for diagnosis. If it is determined not to be suitable for diagnosis, execution proceeds to step S2704. If it is determined to be suitable for diagnosis, execution proceeds to step S2705.

In step S2704, a re-imaging instruction is given to the imaging control device 111 to obtain a captured image suitable for diagnosis. Specifically, an imaging instruction is transmitted to the imaging control device 111 via the operation of the image quality assurance terminal 103. This imaging instruction includes a reason for the imaging instruction input via the operation of the image quality assurance terminal 103, and the priority level of the instruction. The priority level can be specified from, for example, urgent, high, middle, and low. Execution then returns to step S2701.

In step S2705, the captured image displayed on the image quality assurance terminal 103 is determined whether to require additional imaging. For example, if it has been determined that additional imaging is required for reasons such as that abdominal diagnosis is also required, in accordance with the input of an operation, execution proceeds to step S2706. If it has been determined that additional imaging is not required, execution proceeds to step S2707.

The processing of step S2706 is similar to that of step S2704. Next, execution proceeds to step S2707.

In step S2707, the captured image received in step S2702 is transferred to the PACS 104 via the operation of the image quality assurance terminal 103. The transferred captured image is saved in the PACS 104. Execution then returns to step S2701.

The flow of a process of adding imaging protocol information based on an imaging instruction received by the imaging control device 111 during examination is similar to the one described in FIG. 7 in the first embodiment. Only differences are described.

A specific processing flow of step S706 is described in accordance with the flowchart of FIG. 28. Such processing is executed mainly by the imaging control device 111.

First in step S2801, the imaging protocol information candidate extraction unit 2801 extracts candidates for imaging protocol information from an unillustrated imaging protocol information candidate storage unit. Next, execution proceeds to step S2802.

In step S2802, a window 2901 illustrated in FIG. 29 is superimposed and displayed on, for example, the imaging screen 301. As illustrated in an area 2902, the priority level and reason of the imaging instruction stored in the imaging instruction storage unit 206 can be displayed in the window 2901. A list of the candidates for imaging protocol information targeted to be added, the candidates having been extracted in step S2801, is displayed in an area 2903. Next, execution proceeds to step S2803.

In step S2803, it is determined whether to add imaging protocol information in accordance with the input of an operation by an operator considering the content of the imaging instruction displayed in the area 2902 and other various circumstances. If it is determined not to add imaging protocol information, execution proceeds to step S2804. If it is determined to, execution proceeds to step S2805.

In step S2804, the cancellation instruction unit 208 transmits, to the image quality assurance terminal 103, a cancellation instruction indicating information to the effect that imaging based on the imaging instruction has been canceled in response to the input of an operation of pressing a cancel button 2905 via the operating unit 113. Next, execution proceeds to step S707 in FIG. 7.

In step S2805, the operator selects appropriate imaging protocol information from the area 2903 via the operating unit 113, and further determines the imaging protocol information to add at the press of an OK button 2904. At this point in time, a plurality of pieces of imaging protocol information can be selected. Next, execution proceeds to step S707 in FIG. 7.

Specific processing of step S708 in FIG. 7 is similar to the one described in FIG. 9 in the first embodiment.

In step S709, the display of the imaging screen displayed on the display unit 112 is updated. The insertion position of the imaging protocol information for additional imaging varies according to the determination by the position specification unit 215 in step S708. Accordingly, FIGS. 30 and 31 each illustrate an insertion position on the imaging screen. After updating the display, execution returns to step S701.

Figure 30:
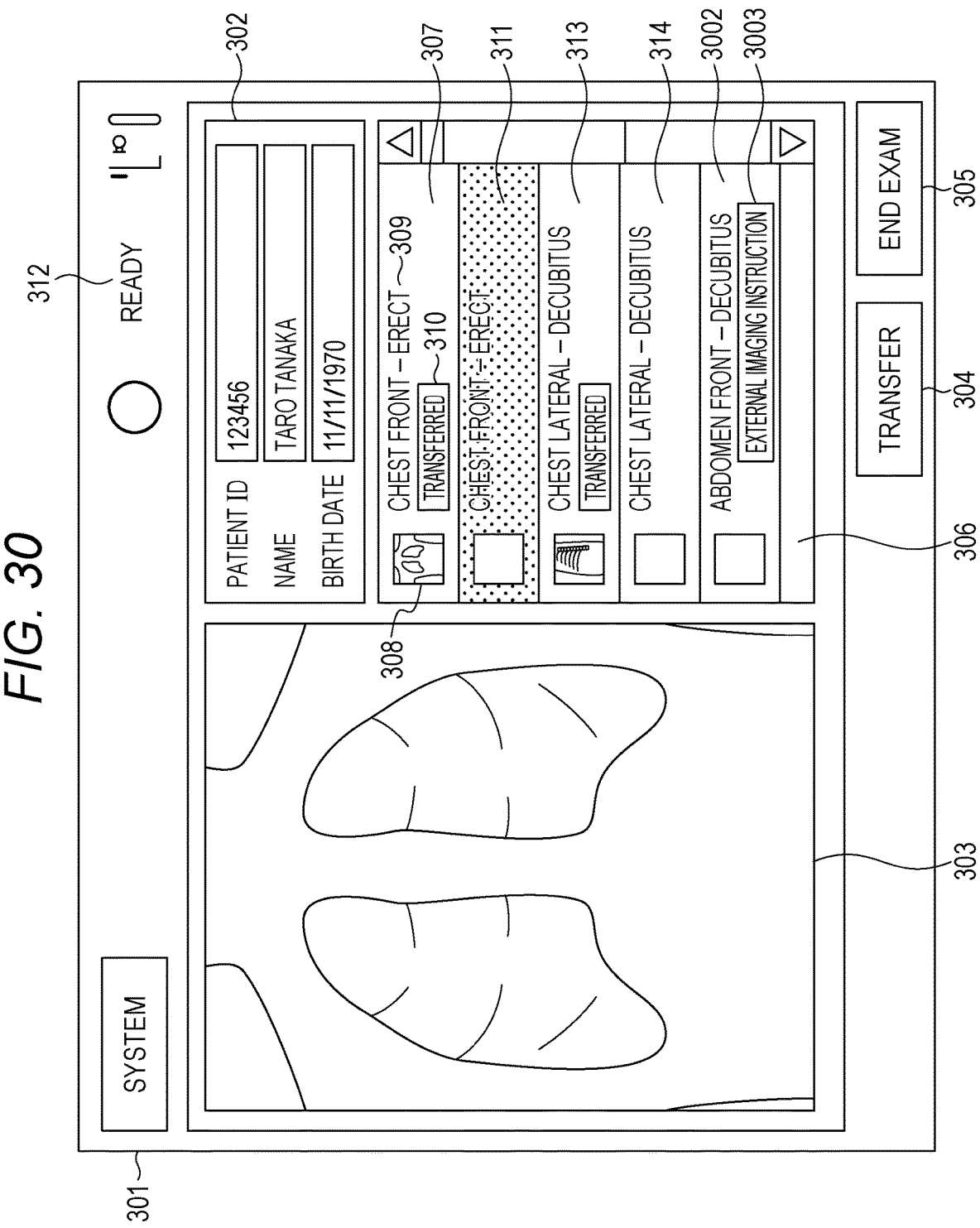
FIG. 30 is a diagram illustrating an example of the imaging screen after the addition of imaging protocol information according to the fifth and sixth embodiments.

FIG. 30 illustrates an example of the imaging screen after the addition of imaging protocol information by an external imaging instruction, the imaging screen being displayed on the display unit 112. The flow until the screen of FIG. 30 is displayed is specifically described. First, what is displayed on the display unit 112 is assumed to be the imaging screen 301 of FIG. 3. In step S505 in FIG. 5, the image captured on the imaging protocol information 307 of FIG. 3 is assumed to be transferred to the image quality assurance terminal 103 in response the input of the operation of pressing the transfer button 304 via the operation of the operating unit 113. It is assumed that the image quality assurance terminal 103 then determines in step S2705 in FIG. 27 that the imaging of the abdomen is also required, and an imaging instruction is transmitted in step S2704. At this point in time, it is assumed that the priority level of the instruction is set to low. After step S706 in FIG. 7, in step S2805 in FIG. 28, imaging protocol information with an imaging region and position—"abdomen front—decubitus" is assumed to be specified. Next, after step S708, first in step S901, there is the imaging protocol information 311 in the imaging ready status. Execution then proceeds to step S902. In step S902, the priority level set in the imaging instruction is low. Execution then proceeds to step S905. In step S905, the imaging region and position—"chest front—erect"—of the imaging protocol information 311 in the imaging ready status is different from the imaging region and position—"abdomen front—decubitus"—of the imaging protocol information specified in step S2805. Execution then proceeds to step S907. In step S907, there is no imaging protocol information with the same imaging region and position "abdomen front—decubitus"—of the imaging protocol information specified in step S2805. Execution then proceeds to step S912. In step S912, the imaging protocol information specified in step S2805 is inserted at the bottom of the imaging protocol information list. As a result of undergoing such a processing flow, what is displayed on the display unit 112 in step S709 is the imaging screen 301 illustrated in FIG. 30. Imaging protocol information 3002 is inserted in step S912. It can be seen that the imaging protocol information 3002 is inserted at the bottom of the imaging protocol information list. Moreover, it can be seen that the imaging region and position of the imaging protocol information 3002 are "abdomen front—decubitus" specified in step S2805. An identifier 3003 indicating that the imaging protocol information 3002 has been added by an external imaging instruction is displayed in the imaging protocol information 3002.

Figure 31:
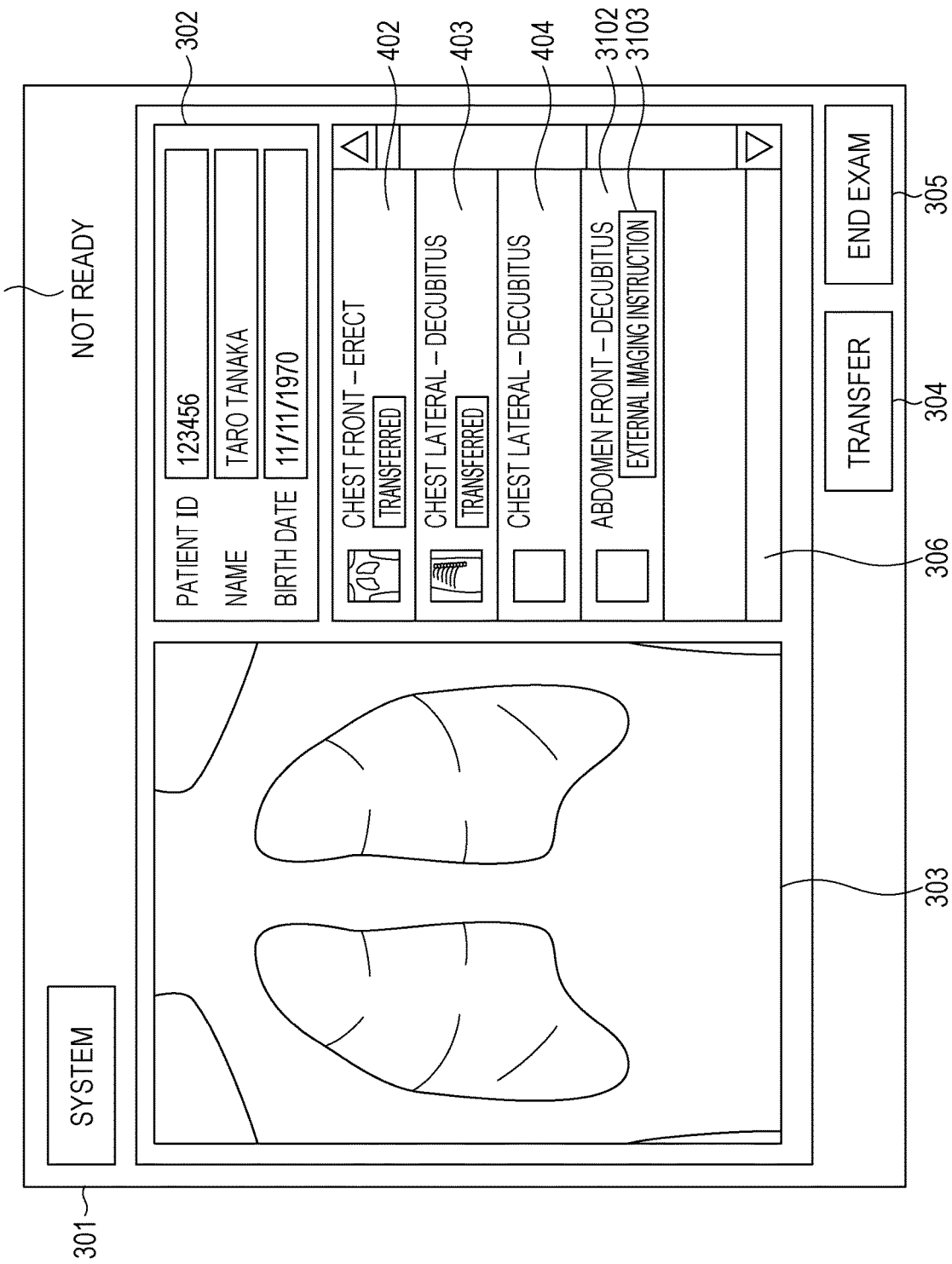
FIG. 31 is a diagram illustrating an example of the imaging screen after the addition of imaging protocol information according to the fifth and sixth embodiments.

FIG. 31 illustrates an example of the imaging screen after the addition of imaging protocol information by an external imaging instruction, the imaging screen being displayed on the display unit 112. The flow until the screen of FIG. 31 is displayed is specifically described. First, what is displayed on the display unit 112 is assumed to be the imaging screen 301 of FIG. 4. In step S505 in FIG. 5, the image captured on the imaging protocol information 402 of FIG. 4 is assumed to be transferred to the image quality assurance terminal 103 at the press of the transfer button 304 via the operation of the operating unit 113. It is assumed that the image quality assurance terminal 103 then determines in step S2705 in FIG. 27 that additional imaging of the abdomen is also required, and an imaging instruction is transmitted in step S2704. At this point in time, it is assumed that the priority level of the instruction is set to low. After step S706 in FIG. 7, in step S2805 in FIG. 28, it is assumed that imaging protocol information with the imaging region and position "abdomen front—decubitus" is assumed to be specified. Next, after step S708, first in step S901, there is no imaging protocol information in the imaging ready status. Execution then proceeds to step S903. In step S903, the priority level set in the imaging instruction is low. Execution then proceeds to step S907. In step S907, there is no imaging protocol information with the same imaging region and position—"abdomen front—decubitus"—as the imaging region and position of the imaging protocol information specified in step S2805. Execution then proceeds to step S912. In step S912, the imaging protocol information specified in step S2805 is inserted at the bottom of the imaging protocol information list. As a result of undergoing such a processing flow, what is displayed on the display unit 112 in step S709 is the imaging screen 301 illustrated in FIG. 31. Imaging protocol information 3102 is inserted in step S912. It can be seen that the imaging protocol information 3102 is inserted at the bottom of the imaging protocol information list. Moreover, the imaging region and position of the imaging protocol information 3102 are "abdomen front—decubitus" specified in step S2805. An identifier 3103 indicating that the imaging protocol information 3102 has been added by an imaging instruction from the outside is displayed in the imaging protocol information 3102.

As described above, according to the fifth embodiment, if an imaging instruction is received from the outside during examination, the screen for selecting additional imaging protocol information is automatically displayed. At this point in time, the priority level and reason of the imaging instruction can be discovered. It is possible to prevent forgetting to add imaging protocol information due to the carelessness of the operator.

Moreover, if imaging protocol information cannot be added since the number of pieces of imaging protocol information and the number of radiation doses in examination order information have reached their upper limits, if imaging protocol information is not added based on a determination by the operator, or if imaging on additional imaging protocol information is not performed based on a determination by the operator, a cancellation instruction is automatically transmitted to an imaging instruction transmission side. Consequently, it is possible to convey information to the effect that the imaging protocol information could not be added without forgetting it.

Moreover, it becomes possible to insert additional imaging protocol information at an appropriate position and take an X-ray preferentially if a high-priority imaging instruction has been received. Furthermore, if the priority level is not high, the additional imaging protocol information is inserted immediately before imaging protocol information with the same imaging region and position. Accordingly, the burden of a change in position on a patient caused by re-imaging can be reduced.

On the whole, inconvenience that can occur when an imaging instruction is received from the outside is eliminated to improve the correctness of an imaging operation.

Sixth Embodiment

Next, a sixth embodiment is described.

Other than differences from the fifth embodiment, the sixth embodiment is similar to the fifth embodiment. Therefore, its description is omitted here except the differences.

The imaging instruction transmitted in step S2704 includes imaging conditions in addition to the items of the fifth embodiment. The imaging conditions include an imaging region and a position.

First in step S2801, the imaging protocol information candidate extraction unit 2801 extracts candidates for imaging protocol information that matches the imaging conditions stored in the imaging instruction storage unit 206 from the unillustrated imaging protocol information candidate storage unit. Next, execution proceeds to step S2802.

In step S2802, a screen 3201 illustrated in FIG. 32 is displayed on the display unit 112. As indicated by a reference numeral 3202, the priority level and reason of the imaging instruction stored in the imaging instruction storage unit 206 can be displayed on the screen 3201. A list of candidates for imaging protocol information targeted to be added, the candidates having been extracted in step S2801, is displayed in a reference numeral 3203. From the example of FIG. 32, it can be seen that only imaging protocol information candidates with an imaging region specified to "abdomen" as the imaging condition in step S2704, which match the imaging region "abdomen," are displayed in the reference numeral 3203. In FIG. 32, the same reference numerals are assigned to the same configurations as those of FIG. 29 used to describe the fifth embodiment. Next, execution proceeds to step S2803.

As described above, according to the sixth embodiment, when an imaging instruction is received from the outside during examination, the screen for selecting additional imaging protocol information is automatically displayed. At this point in time, only imaging protocol information that matches the imaging condition specified by the imaging instruction is displayed on the list of candidates for imaging protocol information, and is selectable. Furthermore, the priority level and reason of the imaging instruction can be discovered. It is possible to prevent a mistake in selecting imaging protocol information with a different imaging condition, and forgetting to add imaging protocol information due to the carelessness of an operator.

Moreover, if imaging protocol information cannot be added since the number of pieces of imaging protocol information and the number of radiation doses in examination order information have reached their upper limits, if imaging protocol information is not added based on a determination by the operator, or if imaging on additional imaging protocol information is not performed based on a determination by the operation, a cancellation instruction is automatically transmitted to an imaging instruction transmission side. Consequently, it is possible to convey information to the effect that the imaging protocol information could not be added without forgetting it.

Moreover, it becomes possible to insert additional imaging protocol information at an appropriate position and take an X-ray preferentially if a high-priority imaging instruction has been received. Furthermore, if the priority level is not high, the additional imaging protocol information is inserted immediately before imaging protocol information with the same imaging region and position. Accordingly, the burden of a change in position on a patient caused by re-imaging can be reduced.

On the whole, inconvenience that can occur when an imaging instruction is received from the outside is eliminated to improve the correctness of an imaging operation.

Other Embodiments

In the above-mentioned embodiments, imaging protocol information is added to examination order information during examination. However, a similar process can be also performed by the examination management unit 252 on pending examination order information with which an examination was started once and then pended before the end. In this case, after the examination order information during examination ends, the display control unit 253 displays a list of examination order information. In parallel with this, the examination management unit 252 identifies pending examination order information to which imaging protocol information has been added at an additional imaging instruction from the outside, among the examinations on the list. The display control unit 253 displays the pending examination order information to which the imaging protocol information has been added in a manner distinguishable from pending examination order information to which an imaging protocol has not been added. Consequently, imaging protocol information can also be added to pending examination order information.

The imaging control device 111 that achieves the above-mentioned functions and processes is a single device. However, the imaging control device 111 can be realized by an imaging control system including a plurality of devices. For example, such an imaging control system can include the sensor 109 that acquires a captured image based on the first imaging protocol information included in the imaging information. For example, the function of acquiring imaging protocol information for additional imaging can be a device shared by a plurality of imaging control systems. The plurality of devices included in the imaging control system does not need to be, for example, in the same hospital or country. The plurality of devices is simply required to be connected to each other by, for example, an Ethernet (registered trademark) cable in a manner capable of communication.

In the above-mentioned embodiments, for example, the image quality assurance terminal 103 transmits additional imaging instruction information. However, this configuration is not limiting. An image display device of the PACS 104 can have the function of the above-mentioned image quality assurance terminal to transmit additional imaging instruction information.

Additional embodiments also include a combination of the above-mentioned embodiments.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, interpretation out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-236743, filed Dec. 3, 2015, which is hereby incorporated by reference herein in its entirety.

What is claimed is:

1. An imaging control device, comprising at least one processor and memory coupled to each other and cooperating to act as:
an examination acquisition unit configured to acquire examination order information including first imaging protocol information including at least imaging region information, an imaging condition, an irradiation condition, an image processing condition, or an output condition, wherein the first imaging protocol information is information used for taking a medical image of a subject;
an output unit configured to output, external to the imaging control device, the medical image obtained based on the first imaging protocol information;
an additional protocol acquisition unit configured to acquire second imaging protocol information used for performing additional imaging to take a medical image of the subject again based on an instruction from an external apparatus that received the output medical image;
a display control unit configured to display the second imaging protocol information together with the first imaging protocol information, and
a receiving unit configured to receive instruction information from external apparatus,
wherein the display control unit determines display and placement of the second imaging protocol information relative to the first imaging protocol information,
further wherein if the instruction information includes information indicating a priority level of imaging, the display control unit controls at least a display indicating that an additional imaging instruction has been given, or a display form of the second imaging protocol information according to the priority level.

2. The imaging control device according to claim 1, wherein the display control unit displays the second imaging protocol information vertically next to the first imaging protocol information upon the additional protocol acquisition unit acquiring the second imaging protocol information in a state where the examination order information including the first imaging protocol information is displayed.

3. The imaging control device according to claim 1, wherein the display control unit displays the first imaging protocol information in a predetermined area on a display screen, and the display control unit displays the second imaging protocol information in addition to the first imaging protocol information in the predetermined area.

4. The imaging control device according to claim 1, wherein the display control unit displays the second imaging protocol information in a manner distinguishable from the first imaging protocol information.

5. The imaging control device according to claim 1, wherein the display control unit displays the second imaging protocol information for additional imaging vertically next to the first imaging protocol information upon the second imaging protocol information being imaging protocol information related to re-imaging on one of a plurality of pieces of the first imaging protocol information in a state where the plurality of pieces of the first imaging protocol information included in the examination order information is sequentially arranged and displayed.

6. The imaging control device according to claim 1, wherein the at least one processor and memory further cooperate to act as:
a receiving unit configured to receive instruction information from the external apparatus; and
a setting unit configured to, upon at least the imaging condition or the irradiation condition having already been set in at least an imaging unit or an irradiation unit respectively, and imaging being unperformed, write at least a new imaging condition or irradiation condition included in the second imaging protocol information over at least the set imaging condition or set irradiation condition to set the overwritten condition in accordance with information indicating a priority level of imaging corresponding to the second imaging protocol information.

7. The imaging control device according to claim 1, wherein the at least one processor and memory further cooperate to act as:
a notification unit configured to notify a user that an additional imaging instruction has been given upon the second imaging protocol information being acquired by the additional protocol acquisition unit or the instruction received from the external apparatus, in a state where the examination order information including the first imaging protocol information is displayed on a display unit.

8. The imaging control device according to claim 7, wherein the notification unit displays, on the display unit, an item for accepting input of an operation of instructing whether to add an imaging protocol together with information indicating that the additional imaging instruction has been given.

9. The imaging control device according to claim 7, wherein the output unit outputs information indicating that the additional imaging has been accepted in response to acceptance of input of an operation of instructing to add an imaging protocol, and outputs information indicating that the additional imaging has been refused in response to acceptance of input of an operation of instructing not to add an imaging protocol.

10. The imaging control device according to claim 1, wherein the at least one processor and memory further cooperate to act as:
a receiving unit configured to receive instruction information from the external apparatus,
wherein the additional protocol acquisition unit acquires the second imaging protocol information for additional imaging based on the instruction information.

11. The imaging control device according to claim 10, wherein if the instruction information includes image identification information, the additional protocol acquisition unit acquires the second imaging protocol information based on imaging protocol information of the medical image identified by the identification information.

12. The imaging control device according to claim 1, the at least one processor and memory further cooperate to act as:
a determination unit configured to determine whether the second imaging protocol information for additional imaging is imaging protocol information related to re-imaging for the first imaging protocol information; and
a failure display unit configured to, upon determination that the second imaging protocol information is the imaging protocol information related to re-imaging, display a display indicating that the captured image corresponding to the first imaging protocol information is a failure.

13. The imaging control device according to claim 1, wherein the at least one processor and memory further cooperate to act as:
an identification unit configured to identify examination order information associated with the acquired second imaging protocol information.

14. An imaging apparatus, comprising at least one processor and memory coupled to each other and cooperating to act as:
an examination acquisition unit configured to acquire examination order information including imaging protocol information including at least imaging region information, an imaging condition, an irradiation condition, an image processing condition, or an output condition, wherein the first imaging protocol information is information used for taking a medical image of a subject;
an output unit configured to output, external to the imaging control device, the medical image obtained based on the imaging protocol information;
an additional protocol acquisition unit configured to acquire second imaging protocol information used for performing additional imaging which is to take a medical image of the subject again based on an instruction from an external apparatus that received the output medical image;
an imaging unit configured to take a medical image of the subject based on the imaging protocol information;
a display control unit configured to display the second imaging protocol information together with the first imaging protocol information, and
a receiving unit configured to receive instruction information from the external apparatus,
wherein the display control unit determines display and placement of the second imaging protocol information relative to the first imaging protocol information,
further wherein if the instruction information includes information indicating a priority level of imaging, the display control unit controls at least a display indicating that an additional imaging instruction has been given, or a display form of the second imaging protocol information according to the priority level.

15. An imaging control method comprising:
acquiring examination order information including first imaging protocol information including at least imaging region information, an imaging condition, an irradiation condition, an image processing condition, or an output condition and examinee information of imaging related to the examination order information, wherein the first imaging protocol information is information used for taking a medical image of a subject;
outputting the medical image obtained based on the first imaging protocol information; and
acquiring second imaging protocol information used for performing additional imaging to take a medical image of the subject again based on an instruction from an external apparatus that received the output medical image;
displaying the second imaging protocol information together with the first imaging protocol information, and
receiving instruction information from the external apparatus,
wherein display and placement of the second imaging protocol information relative to the first imaging protocol information is determined,
further wherein if the instruction information includes information indicating a priority level of imaging, at least a display indicating that an additional imaging instruction has been given, or a display form of the second imaging protocol information according to the priority level is controlled.

16. A non-transitory computer-readable storage medium storing computer executable instructions to cause a computer to execute an imaging control method, the imaging control method comprising:
acquiring examination order information including first imaging protocol information including at least imaging region information, an imaging condition, an irradiation condition, an image processing condition, or an output condition and examinee information of imaging related to the examination order information, wherein the first imaging protocol information is information used for taking a medical image of a subject;
outputting the medical image obtained based on the first imaging protocol information; and
acquiring second imaging protocol information used for performing additional imaging to take a medical image of the subject again based on an instruction from an external apparatus that received the output medical image;
displaying the second imaging protocol information together with the first imaging protocol information, and
receiving instruction information from the external apparatus,
wherein display and placement of the second imaging protocol information relative to the first imaging protocol information is determined, further wherein if the instruction information includes information indicating a priority level of imaging, at least a display indicating that an additional imaging instruction has been given, or a display form of the second imaging protocol information according to the priority level is controlled.

\* \* \* \* \*